(12) United States Patent
Kavanaugh et al.

(10) Patent No.: US 6,656,728 B1
(45) Date of Patent: Dec. 2, 2003

(54) FIBROBLAST GROWTH FACTOR RECEPTOR-IMMUNOGLOBULIN FUSION

(75) Inventors: W. Michael Kavanaugh, Mill Valley, CA (US); Marcus Ballinger, Burlingame, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/499,846

(22) Filed: Feb. 7, 2000

Related U.S. Application Data
(60) Provisional application No. 60/119,002, filed on Feb. 8, 1999.

(51) Int. Cl.$^7$ .................. C12N 15/85; C12N 15/63; C07H 21/04; C07K 14/00; A61K 38/02
(52) U.S. Cl. .................. 435/325; 435/320.1; 536/23.4; 530/350; 530/387.1; 514/2
(58) Field of Search ............... 435/69.7, 69.1, 435/320.1, 325, 252.3, 254.11; 530/350, 387.1, 399; 514/2; 536/23.1, 23.4, 23.5, 23.53

(56) References Cited

U.S. PATENT DOCUMENTS

| | | |
|---|---|---|
| 5,116,964 A | 5/1992 | Capon et al. |
| 5,155,027 A | 10/1992 | Sledziewski et al. |
| 5,229,501 A | 7/1993 | Keifer et al. |
| 5,567,584 A | 10/1996 | Sledziewski et al. |
| 5,707,632 A | 1/1998 | Williams et al. |
| 5,716,805 A | 2/1998 | Srinivasan et al. |
| 5,726,044 A | 3/1998 | Lo et al. |
| 5,750,375 A | 5/1998 | Sledziewski et al. |
| 6,255,454 B1 * | 7/2001 | Keifer et al. ......... 530/350 |

FOREIGN PATENT DOCUMENTS

| | | |
|---|---|---|
| EP | 0 325 224 A2 | 1/1989 |
| EP | 0 314 317 A1 | 5/1989 |
| EP | 0 545 343 A1 | 6/1993 |
| EP | 0 721 983 A1 | 7/1996 |
| EP | 0 801 307 A2 | 3/1997 |
| EP | 0 464 533 A1 | 7/1998 |
| WO | WO 89/02922 | 4/1989 |
| WO | WO 91/00916 | 1/1991 |
| WO | WO 91/08298 | 6/1991 |
| WO | WO 91/11459 | 8/1991 |
| WO | WO 94/04690 | 3/1994 |
| WO | WO 95/21258 | 8/1995 |
| WO | WO 97/28272 | 8/1997 |

OTHER PUBLICATIONS

Ashkenazi, Avi, et al., Protection Against Endotoxic Shock by a Tumor Necrosis Factor Receptor Immunoadhesin, Medical Sciences (1991) 10535–10539, vol. 88.
Bicknell, Roy, et al., Mechanisms and Therapeutic Implications of Angiogenesis, Current Opinion in Oncology (1996) 60–65, vol. 8.
Duncan, Alexander, et al., The binding site for Clq on IgG, Nature (1988) 738–740, vol. 332, No. 21.
Fisher, Charles J., et al., Treatment of Septic Shock with the Tumor Necrosis Factor Receptor:Fc Fusion Protein, The New England Journal of Medicine (1996) 1697–1702, vol. 334, No. 26.
Kiefer, Michael, C., et al., Molecular Cloning of a Human Basic Fibroblast Growth Factor Receptor cDNA and Expression of a Biologically Active Extracellular Domain in a Baculovirus System, Growth Factors (1991) 115–127, vol. 5.
Kim, K. Jin, et al., Inhibition of Vascular Endothelial Growth Factor–Induced Angiogenesis Suppresses Tumour Growth in vivo, Nature (1993) 841–844, vol. 362.
Lenschow, Deborah, et al., Long–Term Survival of Xenogeneic Pancreatic Islet Grafts Induced by CTLA4lg. Science (1992) 789–792, Vol 257.
Linsley, Peter, et al., Immunosuppression in vivo by a Soluble Form of the CTLA–4 T Cell Activation Molecule, Science (1992) 792–794, vol. 257.
Millauer, Birgit, et al., Glioblastoma Growth Inhibited in vivo by a Dominant–Negative Flk–1 Mutant, Nature (1994) 576–579, vol. 367.
Min, Hye Yeong, et al., Urokinase Receptor Antagonists Inhibit Angiogenesis and Primary Tumor Growth in Syngenic Mice, Cancer Research (1996) 2428–2433, vol. 56.
Mohler, Kendall, et al., Soluble Tumor Necrosis Factor (TNF) Receptors are Effective Therapeutic Agents in Lethal Endotoxemia and Function Simultaneously as both TNF Carriers and TNF Antagonists, The Journal of Immunology (1993) 1548–1561, vol. 151, No. 3.
Moreland, Larry W., et al., Treatment of Rheumatoid Arthritis with a Recombinant Human Tumor Necrosis Factor Receptor (p75)–Fe Fusion Protein, The New England Journal of Medicine (1997) 141–147, vol. 337, No. 3.
Moy, Franklin J., et al., Properly Oriented Heparin—Decasaccharie–Induced Dimers Are the Biologically Active Form of Basic Fibroblast Growth Factor, Biochemistry (1997) 4782–4791, vol. 36, No. 16.
Pantoliano, Michael W., et al., Multivalent Ligand–Receptor Binding Interactions in the Fibroblast Growth Factor System Produce a Cooperative Growth Factor and Heparin Mechanism for Receptor Dimerization, Biochemistry (1994) 10229–10248, vol. 33, No. 34.

(List continued on next page.)

Primary Examiner—Elizabeth Kemmerer
Assistant Examiner—Ruixiang Li
(74) Attorney, Agent, or Firm—Leslie T. Henry; Lisa E. Alexander; Robert P. Blackburn

(57) ABSTRACT

The invention relates to compositions and methods for inhibiting cell proliferation, especially angiogenesis. The invention specifically relates to fusions of the extracellular domain of a fibroblast growth factor receptor (FGFR) with a heterologous oligomerization domain, such as that contained in an immunoglobulin, to provide potent FGFR antagonists.

13 Claims, 5 Drawing Sheets

OTHER PUBLICATIONS

Werner, Sabine, et al., Differential Splicing in the Extracellular Region of Fibroblast Growth Factor Receptor 1 Generates Receptor Variants with Different Ligand–Binding Specificities, Molecular and Cellular Biology (1992) 82–88, vol. 12, No. 1.

Xu, Yuanyuan, et al., Residue at Position 331 in the IgG1 and IgG4 $C_H2$ Domains Contributes to Their Differential Ability to Bind and Activate Complement*, (1994) 3469–3474, vol. 269, No. 5.

Galzie et al. (1997) "Fibroblast Growth Factors and Their Receptors," *Biochem. Cell Biol.* 75:669–685.

Duncan et al., "Localization of the Binding Site for the Human High–Affinity Fc Receptor on IgG", *Nature*, (1988) 332(6164):563–564.

* cited by examiner

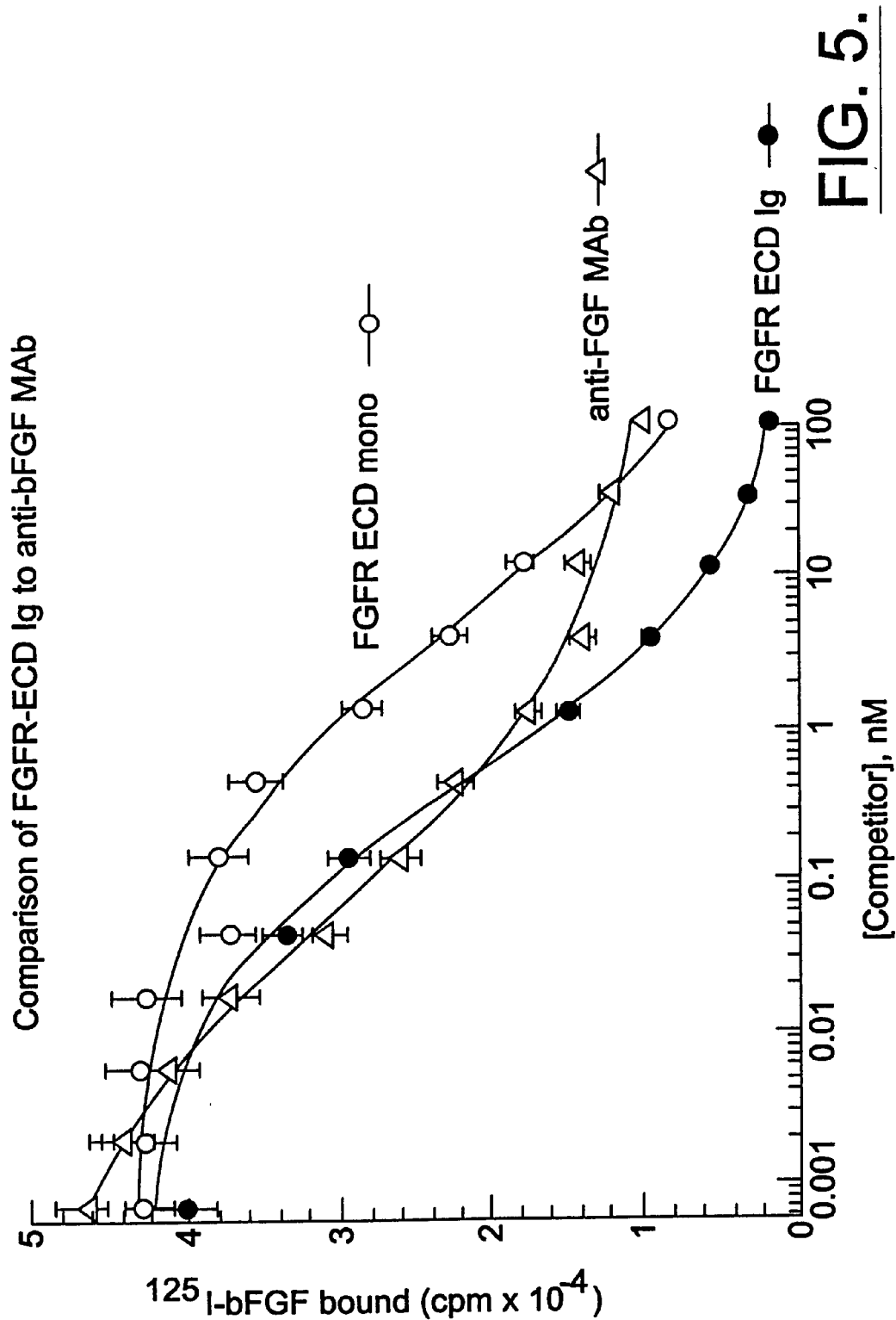

SEQUENCE LISTING

<160> NUMBER OF SEQ ID NOS: 12

<210> SEQ ID NO 1
<211> LENGTH: 1869
<212> TYPE: DNA
<213> ORGANISM: Homo sapiens
<220> FEATURE:
<221> NAME/KEY: CDS
<222> LOCATION: (1)...(1869)

<400> SEQUENCE: 1

```
atg tgg agc tgg aag tgc ctc ctc ttc tgg gct gtg ctg gtc aca gcc      48
Met Trp Ser Trp Lys Cys Leu Leu Phe Trp Ala Val Leu Val Thr Ala
 1               5                  10                  15 aca ctc tgc acc gct agg ccg tcc ccg acc ttg cct gaa caa gcc cag      96
Thr Leu Cys Thr Ala Arg Pro Ser Pro Thr Leu Pro Glu Gln Ala Gln
             20                  25                  30 ccc tgg gga gcc cct gtg gaa gtg gag tcc ttc ctg gtc cac ccc ggt     144
Pro Trp Gly Ala Pro Val Glu Val Glu Ser Phe Leu Val His Pro Gly
         35                  40                  45 gac ctg ctg cag ctt cgc tgt cgg ctg cgg gac gat gtg cag agc atc     192
Asp Leu Leu Gln Leu Arg Cys Arg Leu Arg Asp Asp Val Gln Ser Ile
     50                  55                  60 aac tgg ctg cgg gac ggg gtg cag ctg gcg gaa agc aac cgc acc cgc     240
Asn Trp Leu Arg Asp Gly Val Gln Leu Ala Glu Ser Asn Arg Thr Arg
 65                  70                  75                  80 atc aca ggg gag gag gtg gag gtg cag gac tcc gtg ccc gca gac tcc     288
Ile Thr Gly Glu Glu Val Glu Val Gln Asp Ser Val Pro Ala Asp Ser
                 85                  90                  95 ggc ctc tat gct tgc gta acc agc agc ccc tcc gga agt gac acc acc     336
Gly Leu Tyr Ala Cys Val Thr Ser Ser Pro Ser Gly Ser Asp Thr Thr
            100                 105                 110 tac ttc tcc gtc aat gtt tca gat gct ctc ccc tcc tcg gag gat gat     384
Tyr Phe Ser Val Asn Val Ser Asp Ala Leu Pro Ser Ser Glu Asp Asp
        115                 120                 125 gat gat gat gat gac tcc tct tca gag gag aaa gaa aca gat aac acc     432
Asp Asp Asp Asp Asp Ser Ser Ser Glu Glu Lys Glu Thr Asp Asn Thr
    130                 135                 140 aaa cca aac ccc gta gct cca tat tgg aca tcc cca gaa aag atg gaa     480
Lys Pro Asn Pro Val Ala Pro Tyr Trp Thr Ser Pro Glu Lys Met Glu
145                 150                 155                 160 aag aaa ttg cat gca gtg ccg gct gcc aag aca gtg aag ttc aaa tgc     528
Lys Lys Leu His Ala Val Pro Ala Ala Lys Thr Val Lys Phe Lys Cys
                165                 170                 175 cct tcc agt ggg acc cca aac ccc aca ctg cgc tgg ttg aaa aat ggc     576
Pro Ser Ser Gly Thr Pro Asn Pro Thr Leu Arg Trp Leu Lys Asn Gly
            180                 185                 190 aaa gaa ttc aaa cct gac cac aga att gga ggc tac aag gtc cgt tat     624
Lys Glu Phe Lys Pro Asp His Arg Ile Gly Gly Tyr Lys Val Arg Tyr
        195                 200                 205 gcc acc tgg agc atc ata atg gac tct gtg gtg ccc tct gac aag ggc     672
Ala Thr Trp Ser Ile Ile Met Asp Ser Val Val Pro Ser Asp Lys Gly
    210                 215                 220 aac tac acc tgc att gtg gag aat gag tac ggc agc atc aac cac aca     720
Asn Tyr Thr Cys Ile Val Glu Asn Glu Tyr Gly Ser Ile Asn His Thr
225                 230                 235                 240
```

-continued

| | | |
|---|---|---|
| tac cag ctg gat gtc gtg gag cgg tcc cct cac cgg ccc atc ctg caa<br>Tyr Gln Leu Asp Val Val Glu Arg Ser Pro His Arg Pro Ile Leu Gln<br>245 250 255 | 768 |
| gca ggg ttg ccc gcc aac aaa aca gtg gcc ctg ggt agc aac gtg gag<br>Ala Gly Leu Pro Ala Asn Lys Thr Val Ala Leu Gly Ser Asn Val Glu<br>260 265 270 | 816 |
| ttc atg tgt aag gtg tac agt gac ccg cag ccg cac atc cag tgg cta<br>Phe Met Cys Lys Val Tyr Ser Asp Pro Gln Pro His Ile Gln Trp Leu<br>275 280 285 | 864 |
| aag cac atc gag gtg aat ggg agc aag att ggc cca gac aac ctg cct<br>Lys His Ile Glu Val Asn Gly Ser Lys Ile Gly Pro Asp Asn Leu Pro<br>290 295 300 | 912 |
| tat gtc cag atc ttg aag act gct gga gtt aat acc acc gac aaa gag<br>Tyr Val Gln Ile Leu Lys Thr Ala Gly Val Asn Thr Thr Asp Lys Glu<br>305 310 315 320 | 960 |
| atg gag gtg ctt cac tta aga aat gtc tcc ttt gag gac gca ggg gag<br>Met Glu Val Leu His Leu Arg Asn Val Ser Phe Glu Asp Ala Gly Glu<br>325 330 335 | 1008 |
| tat acg tgc ttg gcg ggt aac tct atc gga ctc tcc cat cac tct gca<br>Tyr Thr Cys Leu Ala Gly Asn Ser Ile Gly Leu Ser His His Ser Ala<br>340 345 350 | 1056 |
| tgg ttg acc gtt ctg gaa gcc ctg gaa gag agg ccg gca gtg atg acc<br>Trp Leu Thr Val Leu Glu Ala Leu Glu Glu Arg Pro Ala Val Met Thr<br>355 360 365 | 1104 |
| tcg ccc ctg tac ctg gag tct aga ggt ggt cta gtg ccg cgc ggc agc<br>Ser Pro Leu Tyr Leu Glu Ser Arg Gly Gly Leu Val Pro Arg Gly Ser<br>370 375 380 | 1152 |
| ggt tcc ccc ggg ttg cag gag ccc aaa tct tgt gac aaa act cac aca<br>Gly Ser Pro Gly Leu Gln Glu Pro Lys Ser Cys Asp Lys Thr His Thr<br>385 390 395 400 | 1200 |
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>405 410 415 | 1248 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>420 425 430 | 1296 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>435 440 445 | 1344 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>450 455 460 | 1392 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>465 470 475 480 | 1440 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>485 490 495 | 1488 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>500 505 510 | 1536 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>515 520 525 | 1584 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>530 535 540 | 1632 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly | 1680 |

|     |     |     |     |     |     |     |     |     |     |     |     |     |     |     |      |
|-----|-----|-----|-----|-----|-----|-----|-----|-----|-----|-----|-----|-----|-----|-----|------|
| 545 |     |     |     |     | 550 |     |     |     |     | 555 |     |     |     | 560 |      |
| cag | ccg | gag | aac | aac | tac | aag | acc | acg | cct | ccc | gtg | ctg | gac | tcc | gac | 1728 |
| Gln | Pro | Glu | Asn | Asn | Tyr | Lys | Thr | Thr | Pro | Pro | Val | Leu | Asp | Ser | Asp |      |
|     |     |     |     | 565 |     |     |     |     | 570 |     |     |     |     | 575 |     |      |
| ggc | tcc | ttc | ttc | ctc | tac | agc | aag | ctc | acc | gtg | gac | aag | agc | agg | tgg | 1776 |
| Gly | Ser | Phe | Phe | Leu | Tyr | Ser | Lys | Leu | Thr | Val | Asp | Lys | Ser | Arg | Trp |      |
|     |     |     | 580 |     |     |     |     | 585 |     |     |     |     | 590 |     |     |      |
| cag | cag | ggg | aac | gtc | ttc | tca | tgc | tcc | gtg | atg | cat | gag | gct | ctg | cac | 1824 |
| Gln | Gln | Gly | Asn | Val | Phe | Ser | Cys | Ser | Val | Met | His | Glu | Ala | Leu | His |      |
|     |     | 595 |     |     |     |     | 600 |     |     |     |     | 605 |     |     |     |      |
| aac | cac | tac | acg | cag | aag | agc | ctc | tcc | ctg | tct | ccg | ggt | aaa | tga |     | 1869 |
| Asn | His | Tyr | Thr | Gln | Lys | Ser | Leu | Ser | Leu | Ser | Pro | Gly | Lys |     |     |      |
|     | 610 |     |     |     |     | 615 |     |     |     |     | 620 |     |     |     |     |      |

<210> SEQ ID NO 2
<211> LENGTH: 622
<212> TYPE: PRT
<213> ORGANISM: Homo sapiens

<400> SEQUENCE: 2

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

```
Lys His Ile Glu Val Asn Gly Ser Lys Ile Gly Pro Asp Asn Leu Pro
    290                 295                 300
Tyr Val Gln Ile Leu Lys Thr Ala Gly Val Asn Thr Thr Asp Lys Glu
305                 310                 315                 320
Met Glu Val Leu His Leu Arg Asn Val Ser Phe Glu Asp Ala Gly Glu
                325                 330                 335
Tyr Thr Cys Leu Ala Gly Asn Ser Ile Gly Leu Ser His His Ser Ala
                340                 345                 350
Trp Leu Thr Val Leu Glu Ala Leu Glu Arg Pro Ala Val Met Thr
                355                 360                 365
Ser Pro Leu Tyr Leu Glu Ser Arg Gly Gly Leu Val Pro Arg Gly Ser
    370                 375                 380
Gly Ser Pro Gly Leu Gln Glu Pro Lys Ser Cys Asp Lys Thr His Thr
385                 390                 395                 400
Cys Pro Pro Cys Pro Ala Pro Glu Leu Leu Gly Gly Pro Ser Val Phe
                405                 410                 415
Leu Phe Pro Pro Lys Pro Lys Asp Thr Leu Met Ile Ser Arg Thr Pro
                420                 425                 430
Glu Val Thr Cys Val Val Val Asp Val Ser His Glu Asp Pro Glu Val
                435                 440                 445
Lys Phe Asn Trp Tyr Val Asp Gly Val Glu Val His Asn Ala Lys Thr
    450                 455                 460
Lys Pro Arg Glu Glu Gln Tyr Asn Ser Thr Tyr Arg Val Val Ser Val
465                 470                 475                 480
Leu Thr Val Leu His Gln Asp Trp Leu Asn Gly Lys Glu Tyr Lys Cys
                485                 490                 495
Lys Val Ser Asn Lys Ala Leu Pro Ala Pro Ile Glu Lys Thr Ile Ser
                500                 505                 510
Lys Ala Lys Gly Gln Pro Arg Glu Pro Gln Val Tyr Thr Leu Pro Pro
    515                 520                 525
Ser Arg Asp Glu Leu Thr Lys Asn Gln Val Ser Leu Thr Cys Leu Val
530                 535                 540
Lys Gly Phe Tyr Pro Ser Asp Ile Ala Val Glu Trp Glu Ser Asn Gly
545                 550                 555                 560
Gln Pro Glu Asn Asn Tyr Lys Thr Thr Pro Val Leu Asp Ser Asp
                565                 570                 575
Gly Ser Phe Phe Leu Tyr Ser Lys Leu Thr Val Asp Lys Ser Arg Trp
                580                 585                 590
Gln Gln Gly Asn Val Phe Ser Cys Ser Val Met His Glu Ala Leu His
    595                 600                 605
Asn His Tyr Thr Gln Lys Ser Leu Ser Leu Ser Pro Gly Lys
    610                 615                 620

<210> SEQ ID NO 3
<211> LENGTH: 1578
<212> TYPE: DNA
<213> ORGANISM: Homo sapiens
<220> FEATURE:
<221> NAME/KEY: CDS
<222> LOCATION: (1)...(1578)

<400> SEQUENCE: 3 atg tgg agc tgg aag tgc ctc ctc ttc tgg gct gtg ctg gtc aca gcc    48
Met Trp Ser Trp Lys Cys Leu Leu Phe Trp Ala Val Leu Val Thr Ala
1               5                   10                  15
```

```
aca ctc tgc acc gct agg ccg tcc ccg acc ttg cct gaa caa gat gct        96
Thr Leu Cys Thr Ala Arg Pro Ser Pro Thr Leu Pro Glu Gln Asp Ala
            20                  25                  30 ctc ccc tcc tcg gag gat gat gat gat gat gac tcc tct tca gag          144
Leu Pro Ser Ser Glu Asp Asp Asp Asp Asp Asp Ser Ser Ser Glu
        35                  40                  45 gag aaa gaa aca gat aac acc aaa cca aac ccc gta gct cca tat tgg      192
Glu Lys Glu Thr Asp Asn Thr Lys Pro Asn Pro Val Ala Pro Tyr Trp
 50                  55                  60 aca tcc cca gaa aag atg gaa aag aaa ttg cat gca gtg ccg gct gcc      240
Thr Ser Pro Glu Lys Met Glu Lys Lys Leu His Ala Val Pro Ala Ala
 65                  70                  75                  80 aag aca gtg aag ttc aaa tgc cct tcc agt ggg acc cca aac ccc aca      288
Lys Thr Val Lys Phe Lys Cys Pro Ser Ser Gly Thr Pro Asn Pro Thr
                85                  90                  95 ctg cgc tgg ttg aaa aat ggc aaa gaa ttc aaa cct gac cac aga att      336
Leu Arg Trp Leu Lys Asn Gly Lys Glu Phe Lys Pro Asp His Arg Ile
            100                 105                 110 gga ggc tac aag gtc cgt tat gcc acc tgg agc atc ata atg gac tct      384
Gly Gly Tyr Lys Val Arg Tyr Ala Thr Trp Ser Ile Ile Met Asp Ser
        115                 120                 125 gtg gtg ccc tct gac aag ggc aac tac acc tgc att gtg gag aat gag      432
Val Val Pro Ser Asp Lys Gly Asn Tyr Thr Cys Ile Val Glu Asn Glu
130                 135                 140 tac ggc agc atc aac cac aca tac cag ctg gat gtc gtg gag cgg tcc      480
Tyr Gly Ser Ile Asn His Thr Tyr Gln Leu Asp Val Val Glu Arg Ser
145                 150                 155                 160 cct cac cgg ccc atc ctg caa gca ggg ttg ccc gcc aac aaa aca gtg      528
Pro His Arg Pro Ile Leu Gln Ala Gly Leu Pro Ala Asn Lys Thr Val
                165                 170                 175 gcc ctg ggt agc aac gtg gag ttc atg tgt aag gtg tac agt gac ccg      576
Ala Leu Gly Ser Asn Val Glu Phe Met Cys Lys Val Tyr Ser Asp Pro
            180                 185                 190 cag ccg cac atc cag tgg cta aag cac atc gag gtg aat ggg agc aag      624
Gln Pro His Ile Gln Trp Leu Lys His Ile Glu Val Asn Gly Ser Lys
        195                 200                 205 att ggc cca gac aac ctg cct tat gtc cag atc ttg aag act gct gga      672
Ile Gly Pro Asp Asn Leu Pro Tyr Val Gln Ile Leu Lys Thr Ala Gly
210                 215                 220 gtt aat acc acc gac aaa gag atg gag gtg ctt cac tta aga aat gtc      720
Val Asn Thr Thr Asp Lys Glu Met Glu Val Leu His Leu Arg Asn Val
225                 230                 235                 240 tcc ttt gag gac gca ggg gag tat acg tgc ttg gcg ggt aac tct atc      768
Ser Phe Glu Asp Ala Gly Glu Tyr Thr Cys Leu Ala Gly Asn Ser Ile
                245                 250                 255 gga ctc tcc cat cac tct gca tgg ttg acc gtt ctg gaa gcc ctg gaa      816
Gly Leu Ser His His Ser Ala Trp Leu Thr Val Leu Glu Ala Leu Glu
            260                 265                 270 gag agg ccg gca gtg atg acc tcg ccc ctg tac ctg gag ggc agc ggt      864
Glu Arg Pro Ala Val Met Thr Ser Pro Leu Tyr Leu Glu Gly Ser Gly
        275                 280                 285 tcc ccc ggg ttg cag gag ccc aaa tct tgt gac aaa act cac aca tgc      912
Ser Pro Gly Leu Gln Glu Pro Lys Ser Cys Asp Lys Thr His Thr Cys
        290                 295                 300 cca ccg tgc cca gca cct gaa ctc ctg ggg gga ccg tca gtc ttc ctc      960
Pro Pro Cys Pro Ala Pro Glu Leu Leu Gly Gly Pro Ser Val Phe Leu
305                 310                 315                 320 ttc ccc cca aaa ccc aag gac acc ctc atg atc tcc cgg acc cct gag     1008
Phe Pro Pro Lys Pro Lys Asp Thr Leu Met Ile Ser Arg Thr Pro Glu
                325                 330                 335
```

```
gtc aca tgc gtg gtg gtg gac gtg agc cac gaa gac cct gag gtc aag    1056
Val Thr Cys Val Val Val Asp Val Ser His Glu Asp Pro Glu Val Lys
        340                 345                 350 ttc aac tgg tac gtg gac ggc gtg gag gtg cat aat gcc aag aca aag    1104
Phe Asn Trp Tyr Val Asp Gly Val Glu Val His Asn Ala Lys Thr Lys
            355                 360                 365 ccg cgg gag gag cag tac aac agc acg tac cgt gtg gtc agc gtc ctc    1152
Pro Arg Glu Glu Gln Tyr Asn Ser Thr Tyr Arg Val Val Ser Val Leu
    370                 375                 380 acc gtc ctg cac cag gac tgg ctg aat ggc aag gag tac aag tgc aag    1200
Thr Val Leu His Gln Asp Trp Leu Asn Gly Lys Glu Tyr Lys Cys Lys
385                 390                 395                 400 gtc tcc aac aaa gcc ctc cca gcc ccc atc gag aaa acc atc tcc aaa    1248
Val Ser Asn Lys Ala Leu Pro Ala Pro Ile Glu Lys Thr Ile Ser Lys
                405                 410                 415 gcc aaa ggg cag ccc cga gaa cca cag gtg tac acc ctg ccc cca tcc    1296
Ala Lys Gly Gln Pro Arg Glu Pro Gln Val Tyr Thr Leu Pro Pro Ser
            420                 425                 430 cgg gat gag ctg acc aag aac cag gtc agc ctg acc tgc ctg gtc aaa    1344
Arg Asp Glu Leu Thr Lys Asn Gln Val Ser Leu Thr Cys Leu Val Lys
    435                 440                 445 ggc ttc tat ccc agc gac atc gcc gtg gag tgg gag agc aat ggg cag    1392
Gly Phe Tyr Pro Ser Asp Ile Ala Val Glu Trp Glu Ser Asn Gly Gln
450                 455                 460 ccg gag aac aac tac aag acc acg cct ccc gtg ctg gac tcc gac ggc    1440
Pro Glu Asn Asn Tyr Lys Thr Thr Pro Pro Val Leu Asp Ser Asp Gly
465                 470                 475                 480 tcc ttc ttc ctc tac agc aag ctc acc gtg gac aag agc agg tgg cag    1488
Ser Phe Phe Leu Tyr Ser Lys Leu Thr Val Asp Lys Ser Arg Trp Gln
            485                 490                 495 cag ggg aac gtc ttc tca tgc tcc gtg atg cat gag gct ctg cac aac    1536
Gln Gly Asn Val Phe Ser Cys Ser Val Met His Glu Ala Leu His Asn
        500                 505                 510 cac tac acg cag aag agc ctc tcc ctg tct ccg ggt aaa tga            1578
His Tyr Thr Gln Lys Ser Leu Ser Leu Ser Pro Gly Lys
            515                 520                 525

<210> SEQ ID NO 4
<211> LENGTH: 525
<212> TYPE: PRT
<213> ORGANISM: Homo sapiens

<400> SEQUENCE: 4

Met Trp Ser Trp Lys Cys Leu Leu Phe Trp Ala Val Leu Val Thr Ala
 1               5                  10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Glu
        35                  40                  45

Glu Lys Glu Thr Asp Asn Thr Lys Pro Asn Pro Val Ala Pro Tyr Trp
 50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
            100                 105                 110

Gly Gly Tyr Lys Val Arg Tyr Ala Thr Trp Ser Ile Ile Met Asp Ser
```

```
              115                 120                 125
Val Val Pro Ser Asp Lys Gly Asn Tyr Thr Cys Ile Val Glu Asn Glu
    130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
        195                 200                 205

Ile Gly Pro Asp Asn Leu Pro Tyr Val Gln Ile Leu Lys Thr Ala Gly
    210                 215                 220

Val Asn Thr Thr Asp Lys Glu Met Glu Val Leu His Leu Arg Asn Val
225                 230                 235                 240

Ser Phe Glu Asp Ala Gly Glu Tyr Thr Cys Leu Ala Gly Asn Ser Ile
                245                 250                 255

Gly Leu Ser His His Ser Ala Trp Leu Thr Val Leu Glu Ala Leu Glu
            260                 265                 270

Glu Arg Pro Ala Val Met Thr Ser Pro Leu Tyr Leu Glu Gly Ser Gly
        275                 280                 285

Ser Pro Gly Leu Gln Glu Pro Lys Ser Cys Asp Lys Thr His Thr Cys
    290                 295                 300

Pro Pro Cys Pro Ala Pro Glu Leu Leu Gly Gly Pro Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
    370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Pro Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Asp Glu Leu Thr Lys Asn Gln Val Ser Leu Thr Cys Leu Val Lys
        435                 440                 445

Gly Phe Tyr Pro Ser Asp Ile Ala Val Glu Trp Glu Ser Asn Gly Gln
    450                 455                 460

Pro Glu Asn Asn Tyr Lys Thr Thr Pro Pro Val Leu Asp Ser Asp Gly
465                 470                 475                 480

Ser Phe Phe Leu Tyr Ser Lys Leu Thr Val Asp Lys Ser Arg Trp Gln
                485                 490                 495

Gln Gly Asn Val Phe Ser Cys Ser Val Met His Glu Ala Leu His Asn
            500                 505                 510

His Tyr Thr Gln Lys Ser Leu Ser Leu Ser Pro Gly Lys
        515                 520                 525

<210> SEQ ID NO 5
```

```
<211> LENGTH: 1494
<212> TYPE: DNA
<213> ORGANISM: Homo sapiens
<220> FEATURE:
<221> NAME/KEY: CDS
<222> LOCATION: (1)...(1494)

<400> SEQUENCE: 5 atg tgg agc tgg aag tgc ctc ctc ttc tgg gct gtg ctg gtc aca gcc      48
Met Trp Ser Trp Lys Cys Leu Leu Phe Trp Ala Val Leu Val Thr Ala
 1               5                  10                  15 aca ctc tgc acc gct agg ccg tcc ccg acc ttg cct gaa caa ccc gta      96
Thr Leu Cys Thr Ala Arg Pro Ser Pro Thr Leu Pro Glu Gln Pro Val
             20                  25                  30 gct cca tat tgg aca tcc cca gaa aag atg gaa aag aaa ttg cat gca     144
Ala Pro Tyr Trp Thr Ser Pro Glu Lys Met Glu Lys Lys Leu His Ala
         35                  40                  45 gtg ccg gct gcc aag aca gtg aag ttc aaa tgc cct tcc agt ggg acc     192
Val Pro Ala Ala Lys Thr Val Lys Phe Lys Cys Pro Ser Ser Gly Thr
     50                  55                  60 cca aac ccc aca ctg cgc tgg ttg aaa aat ggc aaa gaa ttc aaa cct     240
Pro Asn Pro Thr Leu Arg Trp Leu Lys Asn Gly Lys Glu Phe Lys Pro
 65                  70                  75                  80 gac cac aga att ggt ggc tac aag gtc cgt tat gcc acc tgg agc atc     288
Asp His Arg Ile Gly Gly Tyr Lys Val Arg Tyr Ala Thr Trp Ser Ile
                 85                  90                  95 ata atg gac tct gtg gtg ccc tct gac aag ggc aac tac acc tgc att     336
Ile Met Asp Ser Val Val Pro Ser Asp Lys Gly Asn Tyr Thr Cys Ile
            100                 105                 110 gtg gag aat gag tac ggc agc atc aac cac aca tac cag ctg gat gtc     384
Val Glu Asn Glu Tyr Gly Ser Ile Asn His Thr Tyr Gln Leu Asp Val
        115                 120                 125 gtg gag cgg tcc cct cac cgg ccc atc ctg caa gca ggg ttg ccc gcc     432
Val Glu Arg Ser Pro His Arg Pro Ile Leu Gln Ala Gly Leu Pro Ala
    130                 135                 140 aac aaa aca gtg gcc ctg ggt agc aac gtg gag ttc atg tgt aag gtg     480
Asn Lys Thr Val Ala Leu Gly Ser Asn Val Glu Phe Met Cys Lys Val
145                 150                 155                 160 tac agt gac ccg cag ccg cac atc cag tgg cta aag cac atc gag gtg     528
Tyr Ser Asp Pro Gln Pro His Ile Gln Trp Leu Lys His Ile Glu Val
                165                 170                 175 aat ggg agc aag att ggc cca gac aac ctg cct tat gtc cag atc ttg     576
Asn Gly Ser Lys Ile Gly Pro Asp Asn Leu Pro Tyr Val Gln Ile Leu
            180                 185                 190 aag act gct gga gtt aat acc acc gac aaa gag atg gag gtg ctt cac     624
Lys Thr Ala Gly Val Asn Thr Thr Asp Lys Glu Met Glu Val Leu His
        195                 200                 205 tta aga aat gtc tcc ttt gag gac gca ggg gag tat acg tgc ttg gcg     672
Leu Arg Asn Val Ser Phe Glu Asp Ala Gly Glu Tyr Thr Cys Leu Ala
    210                 215                 220 ggt aac tct atc gga ctc tcc cat cac tct gca tgg ttg acc gtt ctg     720
Gly Asn Ser Ile Gly Leu Ser His His Ser Ala Trp Leu Thr Val Leu
225                 230                 235                 240 gaa gcc ctg gaa gag agg ccg gca gtg atg acc tcg ccc ctg tac ctg     768
Glu Ala Leu Glu Glu Arg Pro Ala Val Met Thr Ser Pro Leu Tyr Leu
                245                 250                 255 gag ggc agc ggt tcc ccc ggg ttg cag gag ccc aaa tct tgt gac aaa     816
Glu Gly Ser Gly Ser Pro Gly Leu Gln Glu Pro Lys Ser Cys Asp Lys
            260                 265                 270 act cac aca tgc cca ccg tgc cca gca cct gaa ctc ctg ggg gga ccg     864
Thr His Thr Cys Pro Pro Cys Pro Ala Pro Glu Leu Leu Gly Gly Pro
```

-continued

```
                 275                 280                 285
tca gtc ttc ctc ttc ccc cca aaa ccc aag gac acc ctc atg atc tcc      912
Ser Val Phe Leu Phe Pro Pro Lys Pro Lys Asp Thr Leu Met Ile Ser
    290                 295                 300 cgg acc cct gag gtc aca tgc gtg gtg gtg gac gtg agc cac gaa gac      960
Arg Thr Pro Glu Val Thr Cys Val Val Val Asp Val Ser His Glu Asp
305                 310                 315                 320 cct gag gtc aag ttc aac tgg tac gtg gac ggc gtg gag gtg cat aat     1008
Pro Glu Val Lys Phe Asn Trp Tyr Val Asp Gly Val Glu Val His Asn
                325                 330                 335 gcc aag aca aag ccg cgg gag gag cag tac aac agc acg tac cgt gtg     1056
Ala Lys Thr Lys Pro Arg Glu Glu Gln Tyr Asn Ser Thr Tyr Arg Val
            340                 345                 350 gtc agc gtc ctc acc gtc ctg cac cag gac tgg ctg aat ggc aag gag     1104
Val Ser Val Leu Thr Val Leu His Gln Asp Trp Leu Asn Gly Lys Glu
        355                 360                 365 tac aag tgc aag gtc tcc aac aaa gcc ctc cca gcc ccc atc gag aaa     1152
Tyr Lys Cys Lys Val Ser Asn Lys Ala Leu Pro Ala Pro Ile Glu Lys
    370                 375                 380 acc atc tcc aaa gcc aaa ggg cag ccc cga gaa cca cag gtg tac acc     1200
Thr Ile Ser Lys Ala Lys Gly Gln Pro Arg Glu Pro Gln Val Tyr Thr
385                 390                 395                 400 ctg ccc cca tcc cgg gat gag ctg acc aag aac cag gtc agc ctg acc     1248
Leu Pro Pro Ser Arg Asp Glu Leu Thr Lys Asn Gln Val Ser Leu Thr
                405                 410                 415 tgc ctg gtc aaa ggc ttc tat ccc agc gac atc gcc gtg gag tgg gag     1296
Cys Leu Val Lys Gly Phe Tyr Pro Ser Asp Ile Ala Val Glu Trp Glu
            420                 425                 430 agc aat ggg cag ccg gag aac aac tac aag acc acg cct ccc gtg ctg     1344
Ser Asn Gly Gln Pro Glu Asn Asn Tyr Lys Thr Thr Pro Pro Val Leu
        435                 440                 445 gac tcc gac ggc tcc ttc ttc ctc tac agc aag ctc acc gtg gac aag     1392
Asp Ser Asp Gly Ser Phe Phe Leu Tyr Ser Lys Leu Thr Val Asp Lys
    450                 455                 460 agc agg tgg cag cag ggg aac gtc ttc tca tgc tcc gtg atg cat gag     1440
Ser Arg Trp Gln Gln Gly Asn Val Phe Ser Cys Ser Val Met His Glu
465                 470                 475                 480 gct ctg cac aac cac tac acg cag aag agc ctc tcc ctg tct ccg ggt     1488
Ala Leu His Asn His Tyr Thr Gln Lys Ser Leu Ser Leu Ser Pro Gly
                485                 490                 495 aaa tga                                                              1494
Lys
```

<210> SEQ ID NO 6
<211> LENGTH: 497
<212> TYPE: PRT
<213> ORGANISM: Homo sapiens

<400> SEQUENCE: 6

```
Met Trp Ser Trp Lys Cys Leu Leu Phe Trp Ala Val Leu Val Thr Ala
  1               5                  10                  15

Thr Leu Cys Thr Ala Arg Pro Ser Pro Thr Leu Pro Glu Gln Pro Val
                 20                  25                  30

Ala Pro Tyr Trp Thr Ser Pro Glu Lys Met Glu Lys Lys Leu His Ala
             35                  40                  45

Val Pro Ala Ala Lys Thr Val Lys Phe Lys Cys Pro Ser Ser Gly Thr
         50                  55                  60

Pro Asn Pro Thr Leu Arg Trp Leu Lys Asn Gly Lys Glu Phe Lys Pro
 65                  70                  75                  80
```

-continued

```
Asp His Arg Ile Gly Gly Tyr Lys Val Arg Tyr Ala Thr Trp Ser Ile
             85                  90                  95
Ile Met Asp Ser Val Val Pro Ser Asp Lys Gly Asn Tyr Thr Cys Ile
            100                 105                 110
Val Glu Asn Glu Tyr Gly Ser Ile Asn His Thr Tyr Gln Leu Asp Val
            115                 120                 125
Val Glu Arg Ser Pro His Arg Pro Ile Leu Gln Ala Gly Leu Pro Ala
            130                 135                 140
Asn Lys Thr Val Ala Leu Gly Ser Asn Val Glu Phe Met Cys Lys Val
145                 150                 155                 160
Tyr Ser Asp Pro Gln Pro His Ile Gln Trp Leu Lys His Ile Glu Val
                165                 170                 175
Asn Gly Ser Lys Ile Gly Pro Asp Asn Leu Pro Tyr Val Gln Ile Leu
            180                 185                 190
Lys Thr Ala Gly Val Asn Thr Thr Asp Lys Glu Met Glu Val Leu His
            195                 200                 205
Leu Arg Asn Val Ser Phe Glu Asp Ala Gly Glu Tyr Thr Cys Leu Ala
210                 215                 220
Gly Asn Ser Ile Gly Leu Ser His His Ser Ala Trp Leu Thr Val Leu
225                 230                 235                 240
Glu Ala Leu Glu Glu Arg Pro Ala Val Met Thr Ser Pro Leu Tyr Leu
                245                 250                 255
Glu Gly Ser Gly Ser Pro Gly Leu Gln Glu Pro Lys Ser Cys Asp Lys
            260                 265                 270
Thr His Thr Cys Pro Pro Cys Pro Ala Pro Glu Leu Leu Gly Gly Pro
            275                 280                 285
Ser Val Phe Leu Phe Pro Pro Lys Pro Lys Asp Thr Leu Met Ile Ser
290                 295                 300
Arg Thr Pro Glu Val Thr Cys Val Val Val Asp Val Ser His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
            340                 345                 350
Val Ser Val Leu Thr Val Leu His Gln Asp Trp Leu Asn Gly Lys Glu
            355                 360                 365
Tyr Lys Cys Lys Val Ser Asn Lys Ala Leu Pro Ala Pro Ile Glu Lys
            370                 375                 380
Thr Ile Ser Lys Ala Lys Gly Gln Pro Arg Glu Pro Gln Val Tyr Thr
385                 390                 395                 400
Leu Pro Pro Ser Arg Asp Glu Leu Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
            435                 440                 445
Asp Ser Asp Gly Ser Phe Phe Leu Tyr Ser Lys Leu Thr Val Asp Lys
450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys
```

<210> SEQ ID NO 7
<211> LENGTH: 1578
<212> TYPE: DNA
<213> ORGANISM: Homo sapiens
<220> FEATURE:
<221> NAME/KEY: CDS
<222> LOCATION: (1)...(1578)

<400> SEQUENCE: 7

| | | | | | | | | | | | | | | | | |
|---|---|---|---|---|---|---|---|---|---|---|---|---|---|---|---|---|
| atg | tgg | agc | tgg | aag | tgc | ctc | ctc | ttc | tgg | gct | gtg | ctg | gtc | aca | gcc | 48 |
| Met | Trp | Ser | Trp | Lys | Cys | Leu | Leu | Phe | Trp | Ala | Val | Leu | Val | Thr | Ala | |
| 1 | | | | 5 | | | | | 10 | | | | | 15 | | |
| aca | ctc | tgc | acc | gct | agg | ccg | tcc | ccg | acc | ttg | cct | gaa | caa | gat | gct | 96 |
| Thr | Leu | Cys | Thr | Ala | Arg | Pro | Ser | Pro | Thr | Leu | Pro | Glu | Gln | Asp | Ala | |
| | | 20 | | | | | 25 | | | | | 30 | | | | |
| ctc | ccc | tcc | tcg | gag | gat | gat | gat | gat | gat | gac | tcc | tct | tca | gag | | 144 |
| Leu | Pro | Ser | Ser | Glu | Asp | Asp | Asp | Asp | Asp | Asp | Ser | Ser | Ser | Glu | | |
| | 35 | | | | | 40 | | | | | 45 | | | | | |
| gag | aaa | gaa | aca | gat | aac | acc | aaa | cca | aac | ccc | gta | gct | cca | tat | tgg | 192 |
| Glu | Lys | Glu | Thr | Asp | Asn | Thr | Lys | Pro | Asn | Pro | Val | Ala | Pro | Tyr | Trp | |
| 50 | | | | | 55 | | | | | 60 | | | | | | |
| aca | tcc | cca | gaa | aag | atg | gaa | aag | aaa | ttg | cat | gca | gtg | ccg | gct | gcc | 240 |
| Thr | Ser | Pro | Glu | Lys | Met | Glu | Lys | Lys | Leu | His | Ala | Val | Pro | Ala | Ala | |
| 65 | | | | | 70 | | | | | 75 | | | | | 80 | |
| aag | aca | gtg | aag | ttc | aaa | tgc | cct | tcc | agt | ggg | acc | cca | aac | ccc | aca | 288 |
| Lys | Thr | Val | Lys | Phe | Lys | Cys | Pro | Ser | Ser | Gly | Thr | Pro | Asn | Pro | Thr | |
| | | | 85 | | | | | 90 | | | | | 95 | | | |
| ctg | cgc | tgg | ttg | aaa | aat | ggc | aaa | gaa | ttc | aaa | cct | gac | cac | aga | att | 336 |
| Leu | Arg | Trp | Leu | Lys | Asn | Gly | Lys | Glu | Phe | Lys | Pro | Asp | His | Arg | Ile | |
| | | 100 | | | | | 105 | | | | | 110 | | | | |
| gga | ggc | tac | aag | gtc | cgt | tat | gcc | acc | tgg | agc | atc | ata | atg | gac | tct | 384 |
| Gly | Gly | Tyr | Lys | Val | Arg | Tyr | Ala | Thr | Trp | Ser | Ile | Ile | Met | Asp | Ser | |
| | | 115 | | | | | 120 | | | | | 125 | | | | |
| gtg | gtg | ccc | tct | gac | aag | ggc | aac | tac | acc | tgc | att | gtg | gag | aat | gag | 432 |
| Val | Val | Pro | Ser | Asp | Lys | Gly | Asn | Tyr | Thr | Cys | Ile | Val | Glu | Asn | Glu | |
| 130 | | | | | 135 | | | | | 140 | | | | | | |
| tac | ggc | agc | atc | aac | cac | aca | tac | cag | ctg | gat | gtc | gtg | gag | cgg | tcc | 480 |
| Tyr | Gly | Ser | Ile | Asn | His | Thr | Tyr | Gln | Leu | Asp | Val | Val | Glu | Arg | Ser | |
| 145 | | | | | 150 | | | | | 155 | | | | | 160 | |
| cct | cac | cgg | ccc | atc | ctg | caa | gca | ggg | ttg | ccc | gcc | aac | aaa | aca | gtg | 528 |
| Pro | His | Arg | Pro | Ile | Leu | Gln | Ala | Gly | Leu | Pro | Ala | Asn | Lys | Thr | Val | |
| | | | 165 | | | | | 170 | | | | | 175 | | | |
| gcc | ctg | ggt | agc | aac | gtg | gag | ttc | atg | tgt | aag | gtg | tac | agt | gac | ccg | 576 |
| Ala | Leu | Gly | Ser | Asn | Val | Glu | Phe | Met | Cys | Lys | Val | Tyr | Ser | Asp | Pro | |
| | | | 180 | | | | | 185 | | | | | 190 | | | |
| cag | ccg | cac | atc | cag | tgg | cta | aag | cac | atc | gag | gtg | aat | ggg | agc | aag | 624 |
| Gln | Pro | His | Ile | Gln | Trp | Leu | Lys | His | Ile | Glu | Val | Asn | Gly | Ser | Lys | |
| | | 195 | | | | | 200 | | | | | 205 | | | | |
| att | ggc | cca | gac | aac | ctg | cct | tat | gtc | cag | atc | ttg | aag | act | gct | gga | 672 |
| Ile | Gly | Pro | Asp | Asn | Leu | Pro | Tyr | Val | Gln | Ile | Leu | Lys | Thr | Ala | Gly | |
| | 210 | | | | | 215 | | | | | 220 | | | | | |
| gtt | aat | acc | acc | gac | aaa | gag | atg | gag | gtg | ctt | cac | tta | aga | aat | gtc | 720 |
| Val | Asn | Thr | Thr | Asp | Lys | Glu | Met | Glu | Val | Leu | His | Leu | Arg | Asn | Val | |
| 225 | | | | | 230 | | | | | 235 | | | | | 240 | |
| tcc | ttt | gag | gac | gca | ggg | gag | tat | acg | tgc | ttg | gcg | ggt | aac | tct | atc | 768 |
| Ser | Phe | Glu | Asp | Ala | Gly | Glu | Tyr | Thr | Cys | Leu | Ala | Gly | Asn | Ser | Ile | |
| | | | | 245 | | | | | 250 | | | | | 255 | | |
| gga | ctc | tcc | cat | cac | tct | gca | tgg | ttg | acc | gtt | ctg | gaa | gcc | ctg | gaa | 816 |
| Gly | Leu | Ser | His | His | Ser | Ala | Trp | Leu | Thr | Val | Leu | Glu | Ala | Leu | Glu | |
| | | | 260 | | | | | 265 | | | | | 270 | | | |

```
gag agg ccg gca gtg atg acc tcg ccc ctg tac ctg gag ggc agc ggt      864
Glu Arg Pro Ala Val Met Thr Ser Pro Leu Tyr Leu Glu Gly Ser Gly
        275                 280                 285 tcc ccc ggg ttg cag gag ccc aaa tct tgt gac aaa act cac aca tgc      912
Ser Pro Gly Leu Gln Glu Pro Lys Ser Cys Asp Lys Thr His Thr Cys
    290                 295                 300 cca ccg tgc cca gca cct gaa ctc gag ggg gga ccg tca gtc ttc ctc      960
Pro Pro Cys Pro Ala Pro Glu Leu Glu Gly Gly Pro Ser Val Phe Leu
305                 310                 315                 320 ttc ccc cca aaa ccc aag gac acc ctc atg atc tcc cgg acc cct gag     1008
Phe Pro Pro Lys Pro Lys Asp Thr Leu Met Ile Ser Arg Thr Pro Glu
                325                 330                 335 gtc aca tgc gtg gtg gtg gac gtg agc cac gaa gac cct gag gtc aag     1056
Val Thr Cys Val Val Val Asp Val Ser His Glu Asp Pro Glu Val Lys
            340                 345                 350 ttc aac tgg tac gtg gac ggc gtg gag gtg cat aat gcc aag aca aag     1104
Phe Asn Trp Tyr Val Asp Gly Val Glu Val His Asn Ala Lys Thr Lys
        355                 360                 365 ccg cgg gag gag cag tac aac agc acg tac cgt gtg gtc agc gtc ctc     1152
Pro Arg Glu Glu Gln Tyr Asn Ser Thr Tyr Arg Val Val Ser Val Leu
    370                 375                 380 acc gtc ctg cac cag gac tgg ctg aat ggc aag gag tac aag tgc aag     1200
Thr Val Leu His Gln Asp Trp Leu Asn Gly Lys Glu Tyr Lys Cys Lys
385                 390                 395                 400 gtc tcc aac aaa gcc ctc cca gcc tcc atc gag aaa acc atc tcc aaa     1248
Val Ser Asn Lys Ala Leu Pro Ala Ser Ile Glu Lys Thr Ile Ser Lys
                405                 410                 415 gcc aaa ggg cag ccc cga gaa cca cag gtg tac acc ctg ccc cca tcc     1296
Ala Lys Gly Gln Pro Arg Glu Pro Gln Val Tyr Thr Leu Pro Pro Ser
            420                 425                 430 cgg gat gag ctg acc aag aac cag gtc agc ctg acc tgc ctg gtc aaa     1344
Arg Asp Glu Leu Thr Lys Asn Gln Val Ser Leu Thr Cys Leu Val Lys
        435                 440                 445 ggc ttc tat ccc agc gac atc gcc gtg gag tgg gag agc aat ggg cag     1392
Gly Phe Tyr Pro Ser Asp Ile Ala Val Glu Trp Glu Ser Asn Gly Gln
    450                 455                 460 ccg gag aac aac tac aag acc acg cct ccc gtg ctg gac tcc gac ggc     1440
Pro Glu Asn Asn Tyr Lys Thr Thr Pro Pro Val Leu Asp Ser Asp Gly
465                 470                 475                 480 tcc ttc ttc ctc tac agc aag ctc acc gtg gac aag agc agg tgg cag     1488
Ser Phe Phe Leu Tyr Ser Lys Leu Thr Val Asp Lys Ser Arg Trp Gln
                485                 490                 495 cag ggg aac gtc ttc tca tgc tcc gtg atg cat gag gct ctg cac aac     1536
Gln Gly Asn Val Phe Ser Cys Ser Val Met His Glu Ala Leu His Asn
            500                 505                 510 cac tac acg cag aag agc ctc tcc ctg tct ccg ggt aaa tga             1578
His Tyr Thr Gln Lys Ser Leu Ser Leu Ser Pro Gly Lys
        515                 520                 525

<210> SEQ ID NO 8
<211> LENGTH: 525
<212> TYPE: PRT
<213> ORGANISM: Homo sapiens

<400> SEQUENCE: 8

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30
```

-continued

```
Leu Pro Ser Ser Glu Asp Asp Asp Asp Asp Ser Ser Glu
         35                  40                  45

Glu Lys Glu Thr Asp Asn Thr Lys Pro Asn Pro Val Ala Pro Tyr Trp
         50                  55                  60

Thr Ser Pro Glu Lys Met Glu Lys Lys Leu His Ala Val Pro Ala Ala
 65                  70                  75                  80

Lys Thr Val Lys Phe Lys Cys Pro Ser Ser Gly Thr Pro Asn Pro Thr
                 85                  90                  95

Leu Arg Trp Leu Lys Asn Gly Lys Glu Phe Lys Pro Asp His Arg Ile
                100                 105                 110

Gly Gly Tyr Lys Val Arg Tyr Ala Thr Trp Ser Ile Ile Met Asp Ser
         115                 120                 125

Val Val Pro Ser Asp Lys Gly Asn Tyr Thr Cys Ile Val Glu Asn Glu
         130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
                180                 185                 190

Gln Pro His Ile Gln Trp Leu Lys His Ile Glu Val Asn Gly Ser Lys
         195                 200                 205

Ile Gly Pro Asp Asn Leu Pro Tyr Val Gln Ile Leu Lys Thr Ala Gly
         210                 215                 220

Val Asn Thr Thr Asp Lys Glu Met Glu Val Leu His Leu Arg Asn Val
225                 230                 235                 240

Ser Phe Glu Asp Ala Gly Glu Tyr Thr Cys Leu Ala Gly Asn Ser Ile
                245                 250                 255

Gly Leu Ser His His Ser Ala Trp Leu Thr Val Leu Glu Ala Leu Glu
                260                 265                 270

Glu Arg Pro Ala Val Met Thr Ser Pro Leu Tyr Leu Glu Gly Ser Gly
         275                 280                 285

Ser Pro Gly Leu Gln Glu Pro Lys Ser Cys Asp Lys Thr His Thr Cys
         290                 295                 300

Pro Pro Cys Pro Ala Pro Glu Leu Glu Gly Gly Pro Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Lys
                340                 345                 350

Phe Asn Trp Tyr Val Asp Gly Val Glu Val His Asn Ala Lys Thr Lys
         355                 360                 365

Pro Arg Glu Glu Gln Tyr Asn Ser Thr Tyr Arg Val Val Ser Val Leu
         370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Ser Ile Glu Lys Thr Ile Ser Lys
                405                 410                 415

Ala Lys Gly Gln Pro Arg Glu Pro Gln Val Tyr Thr Leu Pro Pro Ser
                420                 425                 430

Arg Asp Glu Leu Thr Lys Asn Gln Val Ser Leu Thr Cys Leu Val Lys
         435                 440                 445

Gly Phe Tyr Pro Ser Asp Ile Ala Val Glu Trp Glu Ser Asn Gly Gln
```

```
                450               455               460
Pro Glu Asn Asn Tyr Lys Thr Thr Pro Val Leu Asp Ser Asp Gly
465                 470               475               480

Ser Phe Phe Leu Tyr Ser Lys Leu Thr Val Asp Lys Ser Arg Trp Gln
                    485               490               495

Gln Gly Asn Val Phe Ser Cys Ser Val Met His Glu Ala Leu His Asn
                500               505               510

His Tyr Thr Gln Lys Ser Leu Ser Leu Ser Pro Gly Lys
            515               520               525

<210> SEQ ID NO 9
<211> LENGTH: 1494
<212> TYPE: DNA
<213> ORGANISM: Homo sapiens
<220> FEATURE:
<221> NAME/KEY: CDS
<222> LOCATION: (1)...(1494)

<400> SEQUENCE: 9 atg tgg agc tgg aag tgc ctc ctc ttc tgg gct gtg ctg gtc aca gcc      48
Met Trp Ser Trp Lys Cys Leu Leu Phe Trp Ala Val Leu Val Thr Ala
1               5                   10                  15 aca ctc tgc acc gct agg ccg tcc ccg acc ttg cct gaa caa ccc gta      96
Thr Leu Cys Thr Ala Arg Pro Ser Pro Thr Leu Pro Glu Gln Pro Val
                20                  25                  30 gct cca tat tgg aca tcc cca gaa aag atg gaa aag aaa ttg cat gca     144
Ala Pro Tyr Trp Thr Ser Pro Glu Lys Met Glu Lys Lys Leu His Ala
            35                  40                  45 gtg ccg gct gcc aag aca gtg aag ttc aaa tgc cct tcc agt ggg acc     192
Val Pro Ala Ala Lys Thr Val Lys Phe Lys Cys Pro Ser Ser Gly Thr
50                  55                  60 cca aac ccc aca ctg cgc tgg ttg aaa aat ggc aaa gaa ttc aaa cct     240
Pro Asn Pro Thr Leu Arg Trp Leu Lys Asn Gly Lys Glu Phe Lys Pro
65                  70                  75                  80 gac cac aga att ggt ggc tac aag gtc cgt tat gcc acc tgg agc atc     288
Asp His Arg Ile Gly Gly Tyr Lys Val Arg Tyr Ala Thr Trp Ser Ile
                85                  90                  95 ata atg gac tct gtg gtg ccc tct gac aag ggc aac tac acc tgc att     336
Ile Met Asp Ser Val Val Pro Ser Asp Lys Gly Asn Tyr Thr Cys Ile
            100                 105                 110 gtg gag aat gag tac ggc agc atc aac cac aca tac cag ctg gat gtc     384
Val Glu Asn Glu Tyr Gly Ser Ile Asn His Thr Tyr Gln Leu Asp Val
        115                 120                 125 gtg gag cgg tcc cct cac cgg ccc atc ctg caa gca ggg ttg ccc gcc     432
Val Glu Arg Ser Pro His Arg Pro Ile Leu Gln Ala Gly Leu Pro Ala
    130                 135                 140 aac aaa aca gtg gcc ctg ggt agc aac gtg gag ttc atg tgt aag gtg     480
Asn Lys Thr Val Ala Leu Gly Ser Asn Val Glu Phe Met Cys Lys Val
145                 150                 155                 160 tac agt gac ccg cag ccg cac atc cag tgg cta aag cac atc gag gtg     528
Tyr Ser Asp Pro Gln Pro His Ile Gln Trp Leu Lys His Ile Glu Val
                165                 170                 175 aat ggg agc aag att ggc cca gac aac ctg cct tat gtc cag atc ttg     576
Asn Gly Ser Lys Ile Gly Pro Asp Asn Leu Pro Tyr Val Gln Ile Leu
            180                 185                 190 aag act gct gga gtt aat acc acc gac aaa gag atg gag gtg ctt cac     624
Lys Thr Ala Gly Val Asn Thr Thr Asp Lys Glu Met Glu Val Leu His
        195                 200                 205 tta aga aat gtc tcc ttt gag gac gca ggg gag tat acg tgc ttg gcg     672
Leu Arg Asn Val Ser Phe Glu Asp Ala Gly Glu Tyr Thr Cys Leu Ala
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 210 |     |     |     | 215 |     |     |     | 220 |     |     |     |     |     |     |
| ggt | aac | tct | atc | gga | ctc | tcc | cat | cac | tct | gca | tgg | ttg | acc | gtt | ctg | 720 |
| Gly | Asn | Ser | Ile | Gly | Leu | Ser | His | His | Ser | Ala | Trp | Leu | Thr | Val | Leu |     |
| 225 |     |     |     | 230 |     |     |     |     | 235 |     |     |     |     | 240 |     |     |
| gaa | gcc | ctg | gaa | gag | agg | ccg | gca | gtg | atg | acc | tcg | ccc | ctg | tac | ctg | 768 |
| Glu | Ala | Leu | Glu | Glu | Arg | Pro | Ala | Val | Met | Thr | Ser | Pro | Leu | Tyr | Leu |     |
|     |     |     |     | 245 |     |     |     |     | 250 |     |     |     |     | 255 |     |     |
| gag | ggc | agc | ggt | tcc | ccc | ggg | ttg | cag | gag | ccc | aaa | tct | tgt | gac | aaa | 816 |
| Glu | Gly | Ser | Gly | Ser | Pro | Gly | Leu | Gln | Glu | Pro | Lys | Ser | Cys | Asp | Lys |     |
|     |     |     | 260 |     |     |     |     | 265 |     |     |     |     | 270 |     |     |     |
| act | cac | aca | tgc | cca | ccg | tgc | cca | gca | cct | gaa | ctc | gag | ggg | gga | ccg | 864 |
| Thr | His | Thr | Cys | Pro | Pro | Cys | Pro | Ala | Pro | Glu | Leu | Glu | Gly | Gly | Pro |     |
|     |     | 275 |     |     |     |     | 280 |     |     |     |     | 285 |     |     |     |     |
| tca | gtc | ttc | ctc | ttc | ccc | cca | aaa | ccc | aag | gac | acc | ctc | atg | atc | tcc | 912 |
| Ser | Val | Phe | Leu | Phe | Pro | Pro | Lys | Pro | Lys | Asp | Thr | Leu | Met | Ile | Ser |     |
|     | 290 |     |     |     |     | 295 |     |     |     |     | 300 |     |     |     |     |     |
| cgg | acc | cct | gag | gtc | aca | tgc | gtg | gtg | gtg | gac | gtg | agc | cac | gaa | gac | 960 |
| Arg | Thr | Pro | Glu | Val | Thr | Cys | Val | Val | Val | Asp | Val | Ser | His | Glu | Asp |     |
| 305 |     |     |     |     | 310 |     |     |     |     | 315 |     |     |     |     | 320 |     |
| cct | gag | gtc | aag | ttc | aac | tgg | tac | gtg | gac | ggc | gtg | gag | gtg | cat | aat | 1008 |
| Pro | Glu | Val | Lys | Phe | Asn | Trp | Tyr | Val | Asp | Gly | Val | Glu | Val | His | Asn |     |
|     |     |     |     | 325 |     |     |     |     | 330 |     |     |     |     | 335 |     |     |
| gcc | aag | aca | aag | ccg | cgg | gag | gag | cag | tac | aac | agc | acg | tac | cgt | gtg | 1056 |
| Ala | Lys | Thr | Lys | Pro | Arg | Glu | Glu | Gln | Tyr | Asn | Ser | Thr | Tyr | Arg | Val |     |
|     |     |     | 340 |     |     |     |     | 345 |     |     |     |     | 350 |     |     |     |
| gtc | agc | gtc | ctc | acc | gtc | ctg | cac | cag | gac | tgg | ctg | aat | ggc | aag | gag | 1104 |
| Val | Ser | Val | Leu | Thr | Val | Leu | His | Gln | Asp | Trp | Leu | Asn | Gly | Lys | Glu |     |
|     |     | 355 |     |     |     |     | 360 |     |     |     |     | 365 |     |     |     |     |
| tac | aag | tgc | aag | gtc | tcc | aac | aaa | gcc | ctc | cca | gcc | tcc | atc | gag | aaa | 1152 |
| Tyr | Lys | Cys | Lys | Val | Ser | Asn | Lys | Ala | Leu | Pro | Ala | Ser | Ile | Glu | Lys |     |
|     | 370 |     |     |     |     | 375 |     |     |     |     | 380 |     |     |     |     |     |
| acc | atc | tcc | aaa | gcc | aaa | ggg | cag | ccc | cga | gaa | cca | cag | gtg | tac | acc | 1200 |
| Thr | Ile | Ser | Lys | Ala | Lys | Gly | Gln | Pro | Arg | Glu | Pro | Gln | Val | Tyr | Thr |     |
| 385 |     |     |     |     | 390 |     |     |     |     | 395 |     |     |     |     | 400 |     |
| ctg | ccc | cca | tcc | cgg | gat | gag | ctg | acc | aag | aac | cag | gtc | agc | ctg | acc | 1248 |
| Leu | Pro | Pro | Ser | Arg | Asp | Glu | Leu | Thr | Lys | Asn | Gln | Val | Ser | Leu | Thr |     |
|     |     |     |     | 405 |     |     |     |     | 410 |     |     |     |     | 415 |     |     |
| tgc | ctg | gtc | aaa | ggc | ttc | tat | ccc | agc | gac | atc | gcc | gtg | gag | tgg | gag | 1296 |
| Cys | Leu | Val | Lys | Gly | Phe | Tyr | Pro | Ser | Asp | Ile | Ala | Val | Glu | Trp | Glu |     |
|     |     |     | 420 |     |     |     |     | 425 |     |     |     |     | 430 |     |     |     |
| agc | aat | ggg | cag | ccg | gag | aac | aac | tac | aag | acc | acg | cct | ccc | gtg | ctg | 1344 |
| Ser | Asn | Gly | Gln | Pro | Glu | Asn | Asn | Tyr | Lys | Thr | Thr | Pro | Pro | Val | Leu |     |
|     |     | 435 |     |     |     |     | 440 |     |     |     |     | 445 |     |     |     |     |
| gac | tcc | gac | ggc | tcc | ttc | ttc | ctc | tac | agc | aag | ctc | acc | gtg | gac | aag | 1392 |
| Asp | Ser | Asp | Gly | Ser | Phe | Phe | Leu | Tyr | Ser | Lys | Leu | Thr | Val | Asp | Lys |     |
|     | 450 |     |     |     |     | 455 |     |     |     |     | 460 |     |     |     |     |     |
| agc | agg | tgg | cag | cag | ggg | aac | gtc | ttc | tca | tgc | tcc | gtg | atg | cat | gag | 1440 |
| Ser | Arg | Trp | Gln | Gln | Gly | Asn | Val | Phe | Ser | Cys | Ser | Val | Met | His | Glu |     |
| 465 |     |     |     |     | 470 |     |     |     |     | 475 |     |     |     |     | 480 |     |
| gct | ctg | cac | aac | cac | tac | acg | cag | aag | agc | ctc | tcc | ctg | tct | ccg | ggt | 1488 |
| Ala | Leu | His | Asn | His | Tyr | Thr | Gln | Lys | Ser | Leu | Ser | Leu | Ser | Pro | Gly |     |
|     |     |     |     | 485 |     |     |     |     | 490 |     |     |     |     | 495 |     |     |
| aaa | tga |     |     |     |     |     |     |     |     |     |     |     |     |     |     | 1494 |
| Lys |     |     |     |     |     |     |     |     |     |     |     |     |     |     |     |     |

<210> SEQ ID NO 10
<211> LENGTH: 497
<212> TYPE: PRT
<213> ORGANISM: Homo sapiens -continued

```
<400> SEQUENCE: 10

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Pro Val
            20                  25                  30

Ala Pro Tyr Trp Thr Ser Pro Glu Lys Met Glu Lys Lys Leu His Ala
        35                  40                  45

Val Pro Ala Ala Lys Thr Val Lys Phe Lys Cys Pro Ser Ser Gly Thr
50                  55                  60

Pro Asn Pro Thr Leu Arg Trp Leu Lys Asn Gly Lys Glu Phe Lys Pro
65                  70                  75                  80

Asp His Arg Ile Gly Gly Tyr Lys Val Arg Tyr Ala Thr Trp Ser Ile
                85                  90                  95

Ile Met Asp Ser Val Val Pro Ser Asp Lys Gly Asn Tyr Thr Cys Ile
            100                 105                 110

Val Glu Asn Glu Tyr Gly Ser Ile Asn His Thr Tyr Gln Leu Asp Val
        115                 120                 125

Val Glu Arg Ser Pro His Arg Pro Ile Leu Gln Ala Gly Leu Pro Ala
130                 135                 140

Asn Lys Thr Val Ala Leu Gly Ser Asn Val Glu Phe Met Cys Lys Val
145                 150                 155                 160

Tyr Ser Asp Pro Gln Pro His Ile Gln Trp Leu Lys His Ile Glu Val
                165                 170                 175

Asn Gly Ser Lys Ile Gly Pro Asp Asn Leu Pro Tyr Val Gln Ile Leu
            180                 185                 190

Lys Thr Ala Gly Val Asn Thr Thr Asp Lys Glu Met Glu Val Leu His
        195                 200                 205

Leu Arg Asn Val Ser Phe Glu Asp Ala Gly Glu Tyr Thr Cys Leu Ala
210                 215                 220

Gly Asn Ser Ile Gly Leu Ser His His Ser Ala Trp Leu Thr Val Leu
225                 230                 235                 240

Glu Ala Leu Glu Glu Arg Pro Ala Val Met Thr Ser Pro Leu Tyr Leu
                245                 250                 255

Glu Gly Ser Gly Ser Pro Gly Leu Gln Glu Pro Lys Ser Cys Asp Lys
            260                 265                 270

Thr His Thr Cys Pro Pro Cys Pro Ala Pro Glu Leu Glu Gly Gly Pro
        275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Ser Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415
```

```
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
            435                 440                 445
Asp Ser Asp Gly Ser Phe Phe Leu Tyr Ser Lys Leu Thr Val Asp Lys
            450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys

<210> SEQ ID NO 11
<211> LENGTH: 1467
<212> TYPE: DNA
<213> ORGANISM: Homo sapiens
<220> FEATURE:
<221> NAME/KEY: CDS
<222> LOCATION: (1)...(1467)

<400> SEQUENCE: 11 atg tgg agc tgg aag tgc ctc ctc ttc tgg gct gtg ctg gtc aca gcc     48
Met Trp Ser Trp Lys Cys Leu Leu Phe Trp Ala Val Leu Val Thr Ala
1               5                   10                  15 aca ctc tgc acc gct agg ccg tcc ccg acc ttg cct gaa caa ccc gta     96
Thr Leu Cys Thr Ala Arg Pro Ser Pro Thr Leu Pro Glu Gln Pro Val
                20                  25                  30 gct cca tat tgg aca tcc cca gaa aag atg gaa aag aaa ttg cat gca    144
Ala Pro Tyr Trp Thr Ser Pro Glu Lys Met Glu Lys Lys Leu His Ala
            35                  40                  45 gtg ccg gct gcc aag aca gtg aag ttc aaa tgc cct tcc agt ggg acc    192
Val Pro Ala Ala Lys Thr Val Lys Phe Lys Cys Pro Ser Ser Gly Thr
        50                  55                  60 cca aac ccc aca ctg cgc tgg ttg aaa aat ggc aaa gaa ttc aaa cct    240
Pro Asn Pro Thr Leu Arg Trp Leu Lys Asn Gly Lys Glu Phe Lys Pro
65                  70                  75                  80 gac cac aga att ggt ggc tac aag gtc cgt tat gcc acc tgg agc atc    288
Asp His Arg Ile Gly Gly Tyr Lys Val Arg Tyr Ala Thr Trp Ser Ile
                85                  90                  95 ata atg gac tct gtg gtg ccc tct gac aag ggc aac tac acc tgc att    336
Ile Met Asp Ser Val Val Pro Ser Asp Lys Gly Asn Tyr Thr Cys Ile
                100                 105                 110 gtg gag aat gag tac ggc agc atc aac cac aca tac cag ctg gat gtc    384
Val Glu Asn Glu Tyr Gly Ser Ile Asn His Thr Tyr Gln Leu Asp Val
            115                 120                 125 gtg gag cgg tcc cct cac cgg ccc atc ctg caa gca ggg ttg ccc gcc    432
Val Glu Arg Ser Pro His Arg Pro Ile Leu Gln Ala Gly Leu Pro Ala
        130                 135                 140 aac aaa aca gtg gcc ctg ggt agc aac gtg gag ttc atg tgt aag gtg    480
Asn Lys Thr Val Ala Leu Gly Ser Asn Val Glu Phe Met Cys Lys Val
145                 150                 155                 160 tac agt gac ccg cag ccg cac atc cag tgg cta aag cac atc gag gtg    528
Tyr Ser Asp Pro Gln Pro His Ile Gln Trp Leu Lys His Ile Glu Val
                165                 170                 175 aat ggg agc aag att ggc cca gac aac ctg cct tat gtc cag atc ttg    576
Asn Gly Ser Lys Ile Gly Pro Asp Asn Leu Pro Tyr Val Gln Ile Leu
            180                 185                 190 aag act gct gga gtt aat acc acc gac aaa gag atg gag gtg ctt cac    624
Lys Thr Ala Gly Val Asn Thr Thr Asp Lys Glu Met Glu Val Leu His
```

```
                  195                 200                 205
tta aga aat gtc tcc ttt gag gac gca ggg gag tat acg tgc ttg gcg    672
Leu Arg Asn Val Ser Phe Glu Asp Ala Gly Glu Tyr Thr Cys Leu Ala
    210                 215                 220 ggt aac tct atc gga ctc tcc cat cac tct gca tgg ttg acc gtt ctg    720
Gly Asn Ser Ile Gly Leu Ser His His Ser Ala Trp Leu Thr Val Leu
225                 230                 235                 240 gaa gcc ctg gaa gag agg ccg gca gtg atg acc tcg ccc ctg tac ctg    768
Glu Ala Leu Glu Glu Arg Pro Ala Val Met Thr Ser Pro Leu Tyr Leu
                245                 250                 255 gag ccc aaa tct tgt gac aaa act cac aca tgc cca ccg tgc cca gca    816
Glu Pro Lys Ser Cys Asp Lys Thr His Thr Cys Pro Pro Cys Pro Ala
            260                 265                 270 cct gaa ctc gag ggg gga ccg tca gtc ttc ctc ttc ccc cca aaa ccc    864
Pro Glu Leu Glu Gly Gly Pro Ser Val Phe Leu Phe Pro Pro Lys Pro
        275                 280                 285 aag gac acc ctc atg atc tcc cgg acc cct gag gtc aca tgc gtg gtg    912
Lys Asp Thr Leu Met Ile Ser Arg Thr Pro Glu Val Thr Cys Val Val
    290                 295                 300 gtg gac gtg agc cac gaa gac cct gag gtc aag ttc aac tgg tac gtg    960
Val Asp Val Ser His Glu Asp Pro Glu Val Lys Phe Asn Trp Tyr Val
305                 310                 315                 320 gac ggc gtg gag gtg cat aat gcc aag aca aag ccg cgg gag gag cag   1008
Asp Gly Val Glu Val His Asn Ala Lys Thr Lys Pro Arg Glu Glu Gln
                325                 330                 335 tac aac agc acg tac cgt gtg gtc agc gtc ctc acc gtc ctg cac cag   1056
Tyr Asn Ser Thr Tyr Arg Val Val Ser Val Leu Thr Val Leu His Gln
            340                 345                 350 gac tgg ctg aat ggc aag gag tac aag tgc aag gtc tcc aac aaa gcc   1104
Asp Trp Leu Asn Gly Lys Glu Tyr Lys Cys Lys Val Ser Asn Lys Ala
        355                 360                 365 ctc cca gcc tcc atc gag aaa acc atc tcc aaa gcc aaa ggg cag ccc   1152
Leu Pro Ala Ser Ile Glu Lys Thr Ile Ser Lys Ala Lys Gly Gln Pro
    370                 375                 380 cga gaa cca cag gtg tac acc ctg ccc cca tcc cgg gat gag ctg acc   1200
Arg Glu Pro Gln Val Tyr Thr Leu Pro Pro Ser Arg Asp Glu Leu Thr
385                 390                 395                 400 aag aac cag gtc agc ctg acc tgc ctg gtc aaa ggc ttc tat ccc agc   1248
Lys Asn Gln Val Ser Leu Thr Cys Leu Val Lys Gly Phe Tyr Pro Ser
                405                 410                 415 gac atc gcc gtg gag tgg gag agc aat ggg cag ccg gag aac aac tac   1296
Asp Ile Ala Val Glu Trp Glu Ser Asn Gly Gln Pro Glu Asn Asn Tyr
            420                 425                 430 aag acc acg cct ccc gtg ctg gac tcc gac ggc tcc ttc ttc ctc tac   1344
Lys Thr Thr Pro Pro Val Leu Asp Ser Asp Gly Ser Phe Phe Leu Tyr
        435                 440                 445 agc aag ctc acc gtg gac aag agc agg tgg cag cag ggg aac gtc ttc   1392
Ser Lys Leu Thr Val Asp Lys Ser Arg Trp Gln Gln Gly Asn Val Phe
    450                 455                 460 tca tgc tcc gtg atg cat gag gct ctg cac aac cac tac acg cag aag   1440
Ser Cys Ser Val Met His Glu Ala Leu His Asn His Tyr Thr Gln Lys
465                 470                 475                 480 agc ctc tcc ctg tct ccg ggt aaa tga                               1467
Ser Leu Ser Leu Ser Pro Gly Lys
                485

<210> SEQ ID NO 12
<211> LENGTH: 488
<212> TYPE: PRT
<213> ORGANISM: Homo sapiens
```

```
<400> SEQUENCE: 12

Met Trp Ser Trp Lys Cys Leu Leu Phe Trp Ala Val Leu Val Thr Ala
 1               5                  10                  15

Thr Leu Cys Thr Ala Arg Pro Ser Pro Thr Leu Pro Glu Gln Pro Val
                20                  25                  30

Ala Pro Tyr Trp Thr Ser Pro Glu Lys Met Glu Lys Lys Leu His Ala
            35                  40                  45

Val Pro Ala Ala Lys Thr Val Lys Phe Lys Cys Pro Ser Ser Gly Thr
        50                  55                  60

Pro Asn Pro Thr Leu Arg Trp Leu Lys Asn Gly Lys Glu Phe Lys Pro
65                  70                  75                  80

Asp His Arg Ile Gly Gly Tyr Lys Val Arg Tyr Ala Thr Trp Ser Ile
                85                  90                  95

Ile Met Asp Ser Val Val Pro Ser Asp Lys Gly Asn Tyr Thr Cys Ile
                100                 105                 110

Val Glu Asn Glu Tyr Gly Ser Ile Asn His Thr Tyr Gln Leu Asp Val
            115                 120                 125

Val Glu Arg Ser Pro His Arg Pro Ile Leu Gln Ala Gly Leu Pro Ala
        130                 135                 140

Asn Lys Thr Val Ala Leu Gly Ser Asn Val Glu Phe Met Cys Lys Val
145                 150                 155                 160

Tyr Ser Asp Pro Gln Pro His Ile Gln Trp Leu Lys His Ile Glu Val
                165                 170                 175

Asn Gly Ser Lys Ile Gly Pro Asp Asn Leu Pro Tyr Val Gln Ile Leu
                180                 185                 190

Lys Thr Ala Gly Val Asn Thr Thr Asp Lys Glu Met Glu Val Leu His
            195                 200                 205

Leu Arg Asn Val Ser Phe Glu Asp Ala Gly Glu Tyr Thr Cys Leu Ala
        210                 215                 220

Gly Asn Ser Ile Gly Leu Ser His His Ser Ala Trp Leu Thr Val Leu
225                 230                 235                 240

Glu Ala Leu Glu Glu Arg Pro Ala Val Met Thr Ser Pro Leu Tyr Leu
                245                 250                 255

Glu Pro Lys Ser Cys Asp Lys Thr His Thr Cys Pro Pro Cys Pro Ala
                260                 265                 270

Pro Glu Leu Glu Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
            355                 360                 365

Leu Pro Ala Ser Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
```

-continued

```
                    405                 410                 415
Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

FIBROBLAST GROWTH FACTOR RECEPTOR-IMMUNOGLOBULIN FUSION

CROSS-REFERENCE TO RELATED APPLICATION

This application claims the benefit of U.S. Provisional Application No. 60/119,002, filed Feb. 8, 1999.

FIELD OF THE INVENTION

The invention relates to compositions and methods for inhibiting cell proliferation, especially angiogenesis. The invention specifically relates to fusions of the extracellular domain of a fibroblast growth factor receptor (FGFR) with an immunoglobulin (Ig), especially an Ig Fc region, as an FGFR antagonist. The invention also relates to novel FGFR-Ig fusion proteins.

BACKGROUND OF THE INVENTION

Angiogenesis, or development of new blood vessels, is implicated in a host of diseases including tumorigenesis, metastasis and tumor growth, retinopathies, neovascular ocular disorders, and postangioplasty or postatherectomy restenosis (Bicknell et al. (1996) Curr. Opin. Oncol. 8: 60–65; Gariano et al. (1996) Survey Ophthalmol. 40: 481–490; and Wilcox, J. N. (1993) Am. J. Cardiol. 72: 88E–95E).

Expression and secretion of angiogenic factors by tumors has been investigated. It has been suggested that because tumors express multiple angiogenic factors, broad spectrum antagonists of angiogenesis can provide effective means of tumor stabilization. Anti-angiogenic approaches to tumor therapy have been defined to involve interference with growth, migration and differentiation of blood vessels associated with tumor growth. Anti-angiogenic agents have been categorized to include protease inhibitors, modulators of cytokines, heparin-like molecules, and antagonists of vascular growth factors. Growth factor antagonists have been categorized to include heparin-like molecules, angiogenin antagonists, antisense fibroblast growth factor, DS 4152, suramin analogs, and protein-bound saccharide-K (Bicknell et al. (1996) Curr. Opin. Oncol. 8: 60–65).

Various growth factors and growth factor receptors are known to be associated with particular types of tumors. At the molecular level, growth factors and growth factor receptors belong to multi-member families categorized based on structural and functional characteristics. Fibroblast growth factor (FGF) is involved in growth and differentiation of a number of cell types, and can contribute significantly to tumorigenicity. The FGF family includes FGF-1 or acidic FGF (aFGF), FGF-2 or basic FGF (bFGF), FGF-7 or KGF, oncogene products FGF-3 or int-2, hsp/Kaposi-FGF (K-FGF or FGF-4), FGF-5, and FGF-6. These members of the FGF family bind heparin, may exhibit mitogenic activity toward various cells, and may be potent mediators of angiogenesis. (Pontaliano et al. (1994) Biochemistry 33: 10229–10248; Kiefer et al. (1991) Growth Factors 5: 115–127).

FGF receptor (FGFR) includes FGFR1 or flg, FGFR2 or bek, FGFR3 or cek2, and FGFR4 (Kiefer et al. (1991) Growth Factors 5: 115–127). FGFR belongs to the tyrosine kinase family of receptors and to the immunoglobulin (Ig) supergene family. mRNA splicing variants of FGFR exist that produce secreted and transmembrane forms of the receptors with various ligand binding affinities and specificities. In transmembrane forms of the receptor, the tyrosine kinase domain is intracellular and the (Ig)-like domains are extracellular. Both transmembrane and secreted forms bind FGF. Heparin and related compounds promote the interaction between FGF and FGFR by acting as cofactors in dimerization or higher oligomerization of FGFR. The dimerization process is thought to be necessary for activation of FGFR.

FGFR fusion proteins present the possibility of constructing preoligomerized, particularly predimerized forms of FGFR. Such preoligomerized forms would be useful as potent and therapeutically effective inhibitors of FGF-mediated cell proliferation. FGFR antagonists would be especially useful to treat diseases involving angiogenesis.

Monomeric forms of the FGFR extracellular domain have been used to inhibit FGF-mediated events (Kiefer et al. (1991) Growth Factors 5:115–127). However, preoligomerized forms of the FGFR extracellular domain have not been used as FGFR antagonists. Thus, there is a need for providing preoligomerized forms of FGFR extracellular domain as antagonists of FGFR. Given the implicated role of this ligand/receptor system in angiogenesis, and the breadth of involvement of angiogenesis in several malignancies and other disorders, the approach promises a useful tool in providing an effective therapy for such disorders.

Receptor-immunoglobulin (Ig) fusion proteins have been used in the art. For example, an Ig fusion protein with a human tumor necrosis factor receptor has been applied to treatment of rheumatoid arthritis and septic shock (Moreland et al. (1997) New Engl. J Med. 337: 141–147; Fisher et al. (1996) New Engl. J Med. 334: 1697–1702). An Ig fusion protein with urokinase plasminogen activator (uPA) has been used as a uPA receptor antagonist to inhibit angiogenesis and tumor growth (Min et al. (1996) Cancer Res. 56: 2428–2433). WO 95/21258 describes using FGFR-Ig fusion proteins in a method of identifying agonists and antagonists of FGFR. However, construction and use of the specific FGFR-Ig fusion proteins as antagonists of FGFR has not been suggested. Other examples of receptor-Ig fusion proteins include those described in U.S. Pat. Nos. 5,726,044; 5,707,632; and 5,750,375.

SUMMARY OF THE INVENTION

The invention is directed at providing oligomerized forms of FGFR as FGFR antagonists, constructed by fusing extracellular domains of FGFR with heterologous oligomerization domains. Compositions comprising polypeptides and polynucleotides encoding the fusion polypeptides are provided, as well as methods of using the compositions for treating disorders mediated by FGF, FGFR or angiogenesis, such as cancer and other hyperproliferative diseases.

FGFR extracellular domain monomer, FGFR extracellular domain-Ig Fc fusion dimer, and bFGF are compared as competitors of $^{125}$I-bFGF binding to immobilized FGFR receptors. Bound $^{125}$I-bFGF is plotted against a range of concentrations of each competitor.

Figure 2:
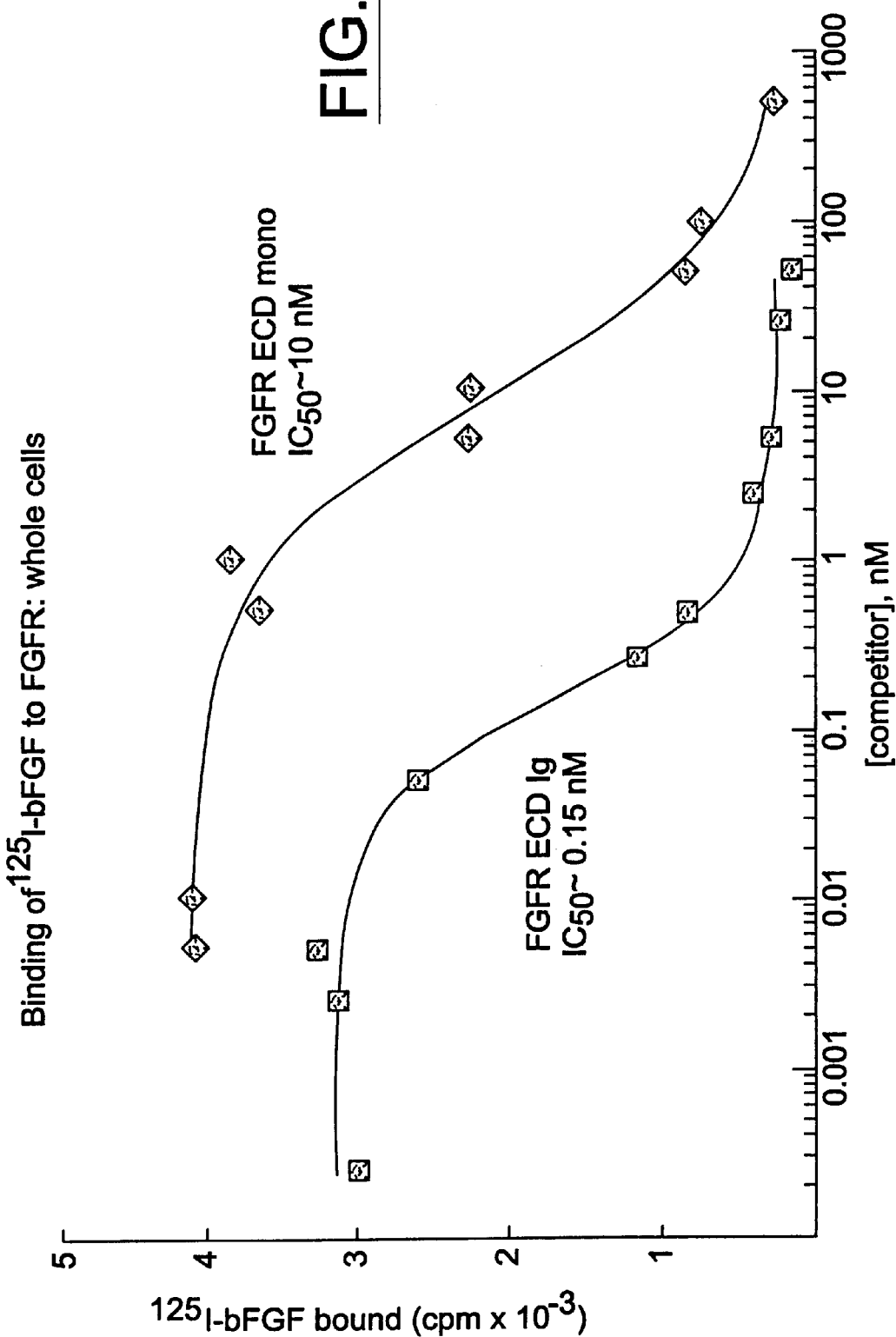

FIG. 2 depicts binding of $^{125}$I-bFGF to FGFR: whole cells.

FGFR extracellular domain monomer and FGFR extracellular domain-Ig Fc fusion dimer are compared as competitors of $^{125}$I-bFGF for binding to stable HEK293 cell lines overexpressing FGFR1. Bound $^{125}$I-bFGF is plotted against a range of concentrations of each competitor.

Figure 3:
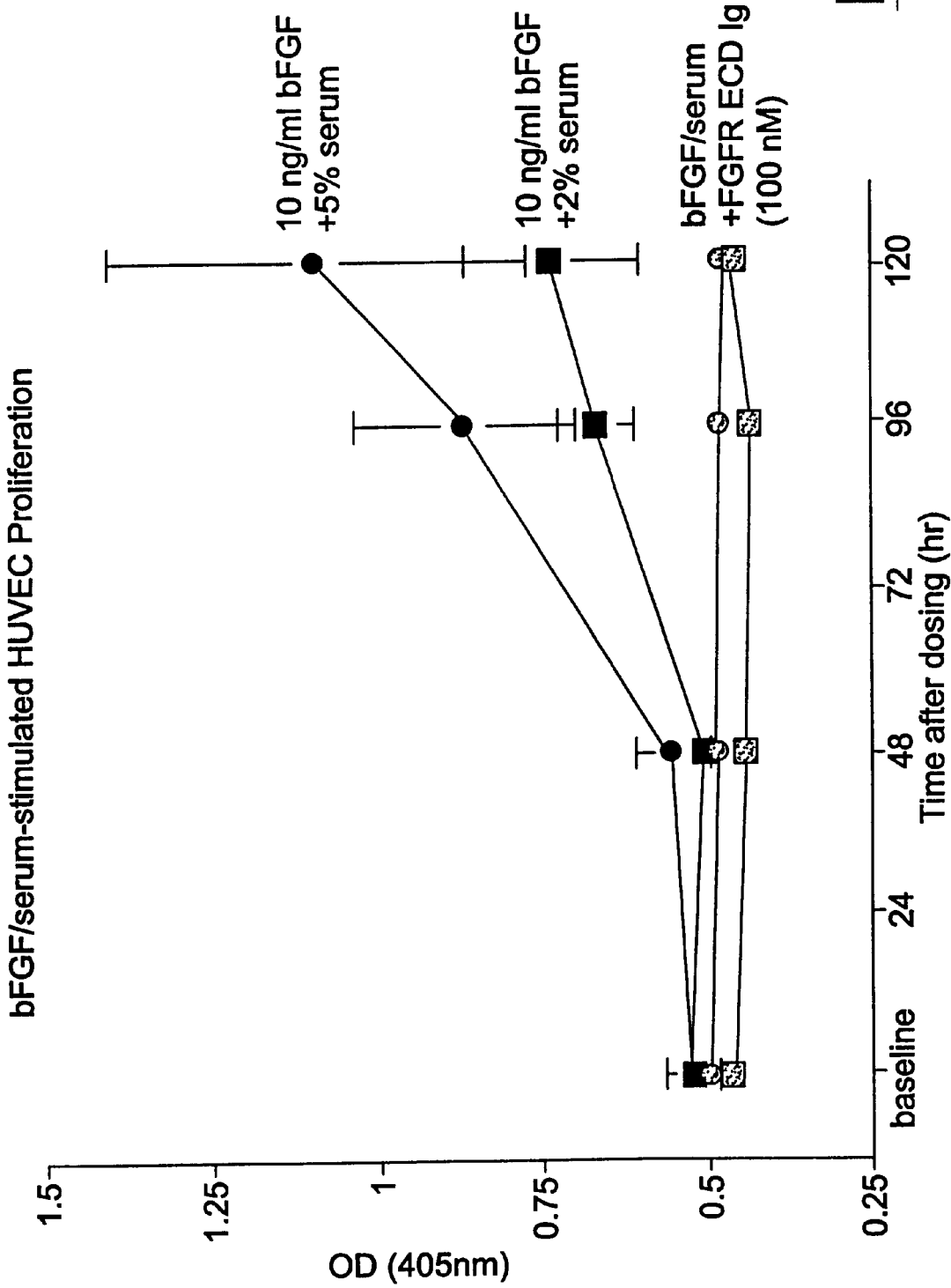

FIG. 3 depicts bFGF/serum stimulated HUVEC proliferation.

FGFR extracellular domain-Ig Fc fusion dimer is tested for its ability to inhibit proliferation of human umbilical vein endothelial cells (HUVEC) in serum- and bFGF-containing media. Optical density (OD) indicating growth is plotted against time after dosing.

Figure 4:
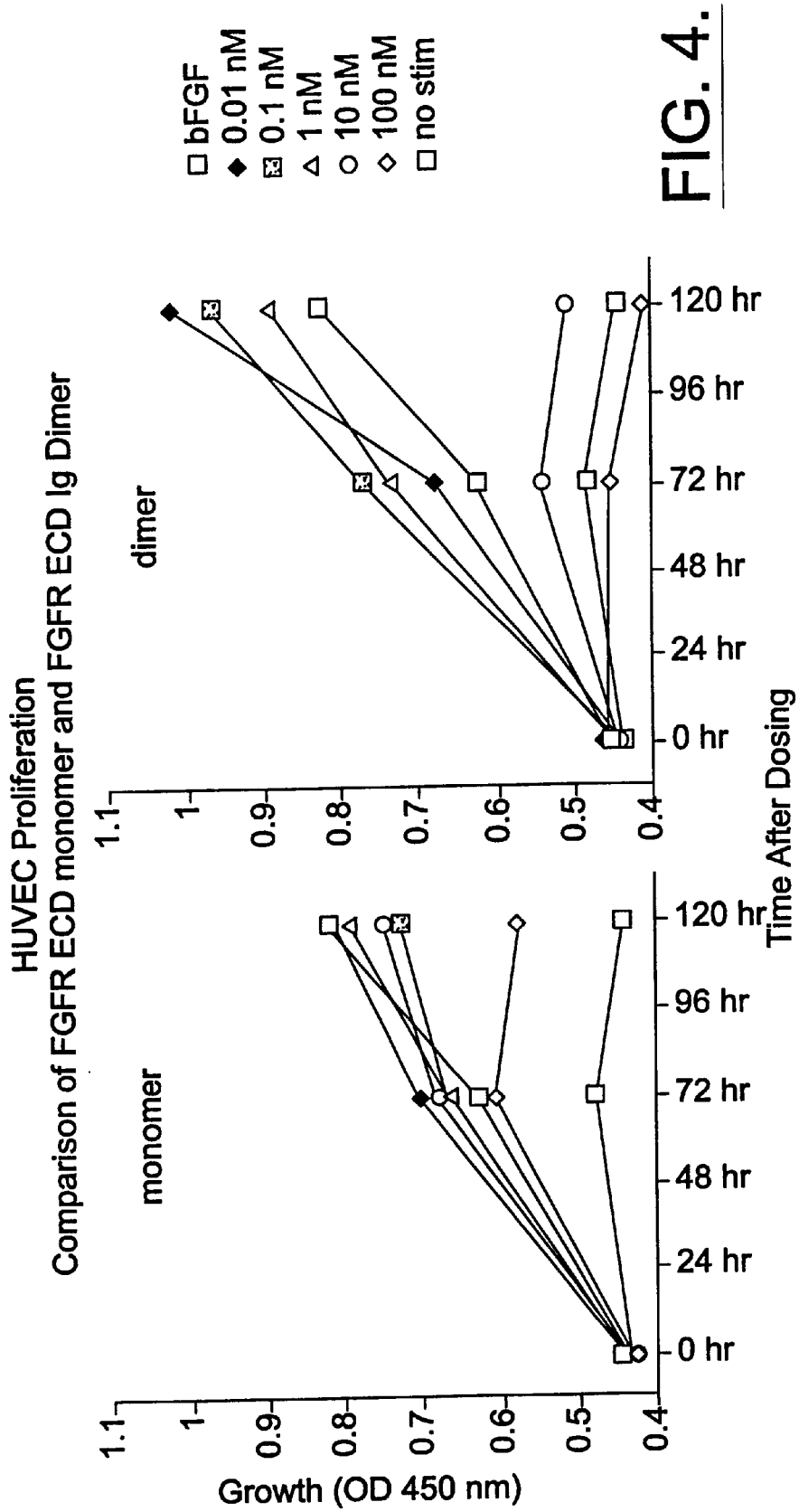

FIG. 4 depicts HUVEC proliferation: comparison of FGFR extracellular domain monomer and FGFR extracellular domain-Ig Fc dimer. FGFR extracellular domain monomer and FGFR extracellular domain-Ig Fc fusion dimer are compared for their ability to inhibit HUVEC proliferation at indicated doses.

FIG. 5 depicts comparison of FGFR extracellular domain-Ig Fc to anti-bFGF Mab. FGFR extracellular domain-Ig Fc fusion protein and an anti-bFGF monoclonal antibody (Mab) are compared as competitors of $^{125}$I-bFGF binding to immobilized FGF receptors. Bound $^{125}$I-bFGF is plotted against a range of concentrations of each competitor.

DETAILED DESCRIPTION OF THE INVENTION

Compositions

The invention is based on means to provide potent FGF receptor (FGFR) antagonists. Dimeric or higher-order oligomeric forms of FGF are required for activation of FGFR, which proceeds through receptor dimerization (Moy et al. (1997) *Biochemistry* 36: 4782–4791; Pontaliano et al. (1994) *Biochemistry* 33: 10229–10248). Accordingly, the invention provides polypeptides capable of forming oligomers of FGFR, particularly dimers. The polypeptides comprise FGFR extracellular domains fused to heterologous oligomerization domains. Such oligomerized FGF receptors are provided as FGFR antagonists with higher potency relative to the monomeric FGFR antagonist. More particularly, the invention provides polypeptides comprising specific FGFR extracellular domains fused to regions of immunoglobulin (Ig) molecules which are known to be capable of forming oligomers with other Ig regions.

"FGFR extracellular domain" as used herein includes that portion of FGFR that is extracellular in native transmembrane forms of the receptor, or is of such extracellular origin, or consists of all or part of the naturally secreted forms of the receptor. It is understood, however, that the extracellular domain could contain other regions of the FGFR receptor (i.e., non-extracellular portions) as long as these portions do not interfere with or significantly alter the function of the extracellular domain that is relevant to the methods described herein.

The FGFR extracellular domain shares homology with the immunoglobulin supergene family. The FGFR extracellular domain contains Ig-like segments. Furthermore, extracellular domains of different members of the FGFR family contain different numbers of Ig-like segments. The Ig-like segments are classified by their position relative to the amino-terminus of the FGF receptor, and by sequence homology to known Ig-like domains. Such classifications are known by a person of ordinary skill in the art. See, for example, Pontaliano et al. (1993), *Biochemistry* 33:10229–10248; Note 1, 10229.

The Ig-like segments are generally designated by numbering according to the relative positions of the segments from the amino terminus of FGFR with three Ig-like domains. Such designations are known by a person of ordinary skill in the art and are used for the purposes of this application, unless indicated otherwise. For example, see Pontaliano et al. (1994) *Biochemistry* 33:10229–10248.

Accordingly, in forms of FGFR having three Ig-like segments, the Ig I segment is classified as the first Ig-like segment of an FGFR extracellular domain from the amino terminus of the molecule, the Ig II segment as the second and the Ig III segment as the third.

In naturally or artificially truncated forms of FGFR which have less than three Ig-like segments by virtue of the truncation of the extracellular domain, the numbering of the Ig-like segments are retained as they were prior to the truncation. The numbers designating the Ig-like segments are not reassigned according to relative positions of the segments from the amino-terminus subsequent to the truncation. Such designations are known in the art and are used for the purposes of this application, unless indicated otherwise. For example, a truncated form of FGFR containing two Ig-like domains due to deletion of a region encompassing the Ig I segment, is referred to as containing the Ig II and Ig III segments, although in this truncated form, the Ig II segment is the first Ig-like segment from the amino-terminus and the Ig III segment is the second.

Extracellular domains of FGFR containing different numbers and types of such Ig-like segments are capable of binding various forms of FGF. The affinity and specificity of this binding is at least partially attributable to the type of Ig-like segment contained within the extracellular domain.

Thus, the invention relates to providing variants of the extracellular domain of FGFR such that FGFR antagonists can be created based on FGF binding capability, -affinity and -specificity.

By "variants" is intended substantially similar sequences. Thus, for nucleotide sequences, variants include those sequences that encode corresponding parts of the fusion polypeptides of the invention, but that differ conservatively because of the degeneracy of the genetic code. These naturally occurring allelic variants can be identified with the use of well-known molecular biology techniques, such as polymerase chain reaction (PCR) and hybridization techniques as outlined below.

Variant nucleotide sequences also include synthetically derived nucleotide sequences that have been generated, for example, by using site-directed mutagenesis but which still encode corresponding parts of the fusion polypeptide sequences provided in the present invention as discussed below. Generally, nucleotide sequence variants of the invention will have at least 70%, preferably at least 80%, more preferably about 90 to 95% or more, and most preferably about 98% or more sequence identity to the provided nucleotide sequence.

A variant polypeptide can differ in amino acid sequence by one or more substitutions, deletions, insertions, inversions, fusions and truncations, or a combination thereof. With respect to the amino acid sequences for various domains of the fusion polypeptides, variants include those domains that are derived from corresponding native domains by deletion (so-called truncation) or addition of one or more amino acids to the N-terminal and/or C-terminal end of the polypeptide; deletion or addition of one or more amino acids at one or more sites in the polypeptide; or substitution of one or more amino acids at one or more sites in the polypeptide. Such variants may result from, for example, genetic polymorphism or from human manipulation. Methods for such manipulations are generally known in the art.

Variants of the FGFR extracellular domain include deletion variants. In one embodiment, amino acid segments that do not contribute to the desired capability, affinity and specificity of binding of FGF are deleted, while those segments that contribute favorably to these functional properties are retained.

Deletion variants also include those in which deletion of particular amino acid segments positively affects the desired affinity and binding of FGF.

Deletion could comprise any segment of the extracellular domain including but not limited to the Ig I segment. In this aspect, the invention provides FGFR extracellular domain fusion polypeptides which lack the Ig I segment. Natural variants of FGFR containing the Ig I segment and those which lack the Ig I segment are capable of binding acidic FGF (aFGF) and basic FGF (bFGF) (Kiefer et al. (1991) *Growth Factors* 5: 115–127.; Johnson and Williams (1993), Adv. *Cancer. Res.* 60:1–41). Thus, the Ig I segment is not necessary for binding of aFGF and bFGF. The Ig I deletion further increases the affinity for aFGF and heparin, protects the core of the molecule from proteolysis, and abrogates the heparin requirement for aFGF binding.

Deletions can range from portions of a segment to deletion of an entire segment. Further, deletions can include one or more deletions in one or more of the Ig-like segments of the FGFR extracellular domain.

The invention further provides fusion polypeptides in which the FGFR extracellular domain lacks the acid box segment. The acid box segment is a known common feature of the FGFR extracellular domain and is characterized by multiple acidic amino acid motifs. For example, see Kiefer et al. (1991) *Growth Factors* 5: 115–127.

The Ig II segment is typically defined as the second Ig-like segment from the amino-terminus of an FGFR with three Ig-like segments. The invention encompasses oligomerized FGFR extracellular domains comprising polypeptides which are variants with respect to the Ig II segment. For example, it is recognized that fusion polypeptides lacking both Ig I and Ig II extracellular segments may have favorable FGF binding characteristics with respect to affinity and specificity of binding and be useful as an FGFR antagonist.

The Ig III segment is typically defined as the third Ig-like segment from the amino-terminus of an FGFR with three Ig-like segments. Sequence variants of the C-terminal half of the Ig III segment are associated with differential FGF binding affinities and specificities. The IIIc variant of the Ig III segment binds aFGF and bFGF with an equal affinity, higher than that for FGF-7. The IIIb variant binds aFGF and FGF-7 with an equal affinity, higher than that for bFGF. The IIIa variant binds bFGF with a higher affinity than that for aFGF. The IIIc variant is the most widely expressed natural variant of the Ig III segment, and its deletion decreases the affinity for all ligands of the receptor. Further descriptions of the Ig IIIa, Ig IIIb and Ig IIIc sequence variants are provided in Werner et al. (1992) *Mol. and Cell Biol.* 12: 82–88, herein incorporated by reference.

The invention provides fusion polypeptides comprising sequence variants of the Ig III segment. The selection of the particular Ig III variants is based on the desired FGF binding affinities and specificities.

More preferred is a fusion polypeptide in which the FGFR extracellular domain comprises the IIIc sequence variant of the Ig III segment. The invention encompasses fusion polypeptides in which the FGFR extracellular domain comprises the IIIa or the IIIb sequence variants of the Ig III segment.

The invention further relates to providing a fusion polypeptide in which the FGFR extracellular domain comprises combinations of the above described variants, including those with deletions of the Ig I segment, those with deletions of the acid box segment and those comprising sequence variants of the Ig III segment.

More specifically, the invention provides human FGFR I extracellular domain fusion polypeptides having the amino acid sequences set forth in SEQ ID NO: 2, SEQ ID NO: 4, SEQ ID NO: 6, SEQ ID NO: 8, SEQ ID NO: 10 and SEQ ID NO: 12. The polypeptides having the sequences set forth in SEQ ID NO: 4, SEQ ID NO: 6, SEQ ID NO: 8, SEQ ID NO: 10 and SEQ ID NO: 12 comprise FGFR extracellular domain deletion variants of human FGFR1; lacking one or more segments as described above. Polynucleotide sequences encoding the above polypeptides are also provided and set forth in SEQ ID NO: 1, SEQ ID NO: 3, SEQ ID NO: 5, SEQ ID NO: 7, SEQ ID NO:9 and SEQ ID NO: 11.

The FGF receptors of the invention also encompass polypeptides and polypeptide fragments that comprise FGFR extracellular domains of other members of the FGFR family, including but not limited to FGFR2, FGFR3 and FGFR4 (Kiefer et al. (1991) *Growth Factors* 5:115–127).

The invention also encompasses FGFR fusion polypeptides comprising other FGFR variants. These variants include substantially homologous FGFR proteins encoded by the same genetic locus, i.e., an allelic variant. The variants also include splicing variants of FGFR. The variants also encompass proteins derived from other genetic loci, but having substantial homology to the provided FGFR. The variants also include proteins substantially homologous to the provided FGFR but derived from another organism (i.e., non-human), i.e., an ortholog. The variants also include proteins substantially homologous that are produced by chemical synthesis. The variants also include proteins substantially homologous that are produced by recombinant methods.

"Homology" refers to the degree of similarity between x and y. The correspondence between the sequence from one form to another can be determined by techniques known in the art. For example, they can be determined by a direct comparison of the sequence information of the polynucleotide. Typically, two sequences, either polynucleotide or polypeptide, are homologous if the sequences exhibit at least 45% sequence identity; more typically, 50% sequence identity; more typically, 55% sequence identity; more typically, 60% sequence identity; more typically, 65% sequence identity; even more typically, 70% sequence identity. Usually, two sequences are homologous if the sequences exhibit at least 75% sequence identity; more usually, 80% sequence identity; even more usually, 85% sequence identity; even more usually, 90% sequence identity; and even more usually, 95% sequence identity.

Thus, the invention encompasses polynucleotides having 75%, preferably 80%, more preferably 85%, even more preferably 90%, and most preferably 95% or greater sequence identity to the polynucleotide sequences set forth in SEQ ID NOs: 1, 3, 5, 7, 9, and 11. The invention further encompasses polypeptides having 75%, preferably 80%, more preferably 85%, even more preferably 90%, and most preferably 95% or greater sequence identity to the polypeptide sequences set forth in SEQ ID NOs: 2, 4, 6, 8, 10, and 12).

Alternatively, homology can be determined by hybridization of the polynucleotides under conditions which form stable duplexes between homologous regions. Stable duplexes are those, for example, which would withstand digestion with a single-stranded specific nuclease(s), such as $S_1$. Such duplexes can be analyzed by various methods, such as size determination of digested fragments.

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. (1989) *Molecular Cloning: A Laboratory Manual*, $2^{nd}$ ed., Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 12° C. to 20° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook et al., above at page 9.50.

Variables to consider when performing, for example, a Southern blot are (1) the complexity of the DNA being blotted and (2) the homology between the probe and the sequences being detected. The total amount of the fragment (s) to be studied can vary a magnitude of 10, from 0.1 to 1 μg for a plasmid or phage digest to 10-9 to 10-8 μg for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 μg of yeast DNA, blotting for two hours, and hybridizing for 4–8 hours with a probe of $10^8$ cpm/μg. For a single-copy mammalian gene a conservative approach would start with 10 μg of DNA, blot overnight, and hybridize overnight in the presence of 10% dextran sulfate using a probe of greater than $10^8$ cpm/μg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log 10C_i)+0.4[\%G+C)]-0.6(\%\text{formamide})-600/n-1.5(\%\text{ mismatch})$$

where $C_i$ is the salt concentration (monovalent ions) and n is the length of the hybrid in base pairs (slightly modified from Meinkoth and Wahl, (1984) *Anal. Biochem.* 138: 267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe which is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology and between the probe and the target fragment are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel.

To determine the percent homology of two amino acid sequences, or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses fusion polypeptides having a lower degree of identity than those described above, but having sufficient similarity so as to perform one or more of the same functions performed by the fusion polypeptides of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991). Preferred computer program methods to determine identity and similarity between two sequences include, but are not limited to, GCG program package (Devereux, J., et al. (1984) *Nucleic Acids Res.* 12(1):387), BLASTP, BLASTN, FASTA (Atschul, S.F. et al. (1990) *J. Molec. Biol.* 215:403).

A variant can differ in amino acid sequence by one or more substitutions, deletions, insertions, inversions, fusions, and truncations or a combination of any of these.

Variant polypeptides can be fully functional or can lack function in one or more activities. Thus, in the present case, functions affected by variations include FGF binding capability, FGF binding affinity, FGF binding specificity, heparin binding, inhibition of FGF-stimulated cell proliferation, inhibition of FGF-mediated disorders, inhibition of FGFR-mediated disorders, inhibition of angiogenesis-mediated disorders, and inhibition of cancer and other hyperproliferative disorders.

Fully functional variants typically contain only conservative variation or variation in non-critical residues or in non-critical regions. Functional variants can also contain substitution of similar amino acids which result in no change or an insignificant change in function. Alternatively, such substitutions may positively or negatively effect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the receptor polypeptide. This includes preventing immunogenicity from pharmaceutical formulations by preventing protein aggregation.

Useful variations include alteration of ligand binding characteristics. For example, one specific embodiment encompasses fusion polypeptide dimers that bind aFGF and bFGF with equal affinity. A further embodiment encompasses fusion polypeptide dimers that bind aFGF and bFGF with equal affinity, but with higher than that for FGF-7. Another embodiment encompasses fusion polypeptide dimers that bind aFGF and bFGF with high affinity.

Another useful variation is one that provides for a protease cleavage site between the extracellular domain of FGFR and the Ig portion of the fusion polypeptide. While constructs containing the cleavage sites are not suited for in vivo use due to the presence of the cleavage site, they are useful as experimental controls. One resulting product from utilizing this cleavage site, is FGFR extracellular domain monomer which is useful as a control in assessing the functional characteristics of the corresponding FGFR extracellular domain-Ig dimer without the cleavage site.

The invention provides polypeptides comprising FGFR extracellular domains fused to heterologous oligomerization domains. By "heterologous oligomerization domain" is intended that domain of a polypeptide of the invention which is not naturally associated with the extracellular domain of the polypeptide, and is capable of forming oligomers, which are at least dimers, with other polypeptides. Specific examples of such heterologous oligomerization domains include, but are not limited to, the Fc region of an immunoglobulin molecule; the hinge region of an immunoglobulin molecule; the CH1 region of an immunoglobulin molecule; the CH2 region of an immunoglobulin molecule; the CH3 region of an immunoglobulin molecule; the CH4 region of an immunoglobulin molecule; the light chain of an immunoglobulin molecule; and a peptide comprising a leucine zipper motif.

Leucine zipper motifs are known in the art, and are typically found in some of the DNA-binding proteins. Leucine zippers are formed from a region of a-helix that contain at least four leucines, each leucine separated by six amino acids from one another (i.e., Leu-$X_6$-Leu-$X_6$-Leu-$X_6$-Leu, where X is any common amino acid). See Devlin (1997) :110–111, Textbook of Biochemistry with Clinical Correlations, Fourth Edition, John Wiley and Sons, Inc.

Examples of utilizing various immunoglobulin domains for constructing oligomeric fusion proteins are known in the art. See, for example, EP-A 0464 533 and U.S. Pat. No. 5,726,044 which describe fusion proteins comprising immunoglobulin Fc regions. See also U.S. Pat. No. 5,750,375 which describes fusion proteins comprising various heavy chain domains, as well as light chain kappa.

The heavy chain Fc region of an immunoglobulin molecule which contains the hinge region, but not the CH1 region of the heavy chain, is useful in therapy and diagnosis; and its incorporation into a protein results, for example, in improved pharmacokinetic properties of the protein. For example, see EP-A 0232 262. In drug discovery applications, human proteins have been fused with Fc portions for the purpose of high-throughput screening assays to identify antagonists. Bennett et al. (1995) *Journal of Molecular Recognition* 8:52–58 and Johanson et al. (1995) *The Journal of Biological Chemistry* 270, 16:9459–9471. This invention encompasses soluble fusion proteins containing a receptor polypeptide and various portions of the constant regions of heavy or light chains of immunoglobulins of various subclass (IgG, IgD, IgM, IgA, IgE). Preferred as immunoglobulin is the constant part of the heavy chain of human IgG, particularly IgG1, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

Furthermore, the proteins of the invention are generally designed to eliminate or at least minimize the contribution of the Ig Fc fusion protein to immunogenic responses. To this end, native or mutated Ig Fc portions are preferred which have low or diminished affinity for Fc receptors, and have diminished capacities for interaction with complement; Duncan and Winter (1988) *Nature* 332: 738–740; Xu et al. (1994) *J Biol. Chem.* 269: 3469–3474. For example, mutations of amino acids corresponding to Leu 235 and Pro 331 of human IgGI to Glu and Ser respectively, are provided. More specifically, these mutations are provided as set forth in SEQ ID NOs: 7 and 8(constructs #4) and SEQ ID NOs: 9 and 10 (construct #5), and described in more detail in Example 6 below.

In order to express any of the fusion proteins of the invention in a secreted form, a signal peptide is typically contained at the N-terminus of the fusion protein. Generally, the signal peptide that is native to the FGFR extracellular domain is comprised by the fusion proteins of the invention. Alternatively, signal peptides that are heterologous with respect to the extracellular domain may be used.

Heparin is known to be required for optimal FGF binding to FGFR. Thus, in constructing the fusion proteins, the heparin binding site is generally retained as part of the FGFR extracellular domain.

Methods for testing the function of the fusion proteins of the invention include, but are not limited to, the following methods, herein incorporated by reference: in vitro and in situ growth factor binding assays (Pontaliano et al. (1994) *Biochemistry* 33:10229–10248; Kiefer et al (1991) *Growth Factors* 5:115–127; U.S. Pat. No. 5,229,501); cell proliferation assays (U.S. Pat. No. 5,229,501; WST cell proliferation assay, Boehringer Mannheim); in vivo and ex vivo assessments of angiogenesis (Min et al. (1996) *Cancer Res.* 56:2428–2433; Bickness et aL (1996) *Curr. Opin. Oncol.* 8: 60–65) and assessments of tumor growth (Kim et al. (1993) *Nature* 362:841–844; Millauer et al. (1993) *Nature* 367:576–579).

It is understood that other methodologies associated with particular pathologies, biological conditions or processes may be employed when applicable to testing the fusion proteins of the invention. Examples of such methodologies include molecular biological, immunochemical, histochemical and morphological assessments relevant to cell proliferation in restenosis (Wilcox J., (1993), *Am. J Cardiol.* 72:88E–95E) and ocular diseases (Gariano et al. (1996) *Survey Ophthalm.* 40:481–490). Additional methodologies for assessing vascular density and tumor growth; biochemical assays utilizing markers of angiogenesis, and in vivo methods of assessing therapeutic effects of antiangiogenic agents disclosed by Bickness et al. (1996) *Curr. Opin. Oncol.* 8:60–65, may also be employed in testing the fusion proteins of the invention, and are herein incorporated by reference.

Polynucleotide Constructs and Host Cells

DNA constructs encoding the FGFR fusion polypeptides of the invention, DNA constructs capable of expressing the FGFR fusion polypeptides, and host cells containing or capable of expressing such constructs are also provided by the invention.

Routine techniques for the construction of the vectors comprising the fusion proteins of the present invention are well-known to those of ordinary skill in the art and can be found in such references as Sambrook et al., *Molecular Cloning: A Laboratory Manual*, $2^{nd}$ ed (Cold Spring Harbor, New York, 1989). A variety of strategies are available for ligating fragments of DNA, the choice of which depends on the nature of the termini of the DNA fragments and which choices can be readily made by those of skill in the art. Generally, and unless otherwise specified, the 3' end of the DNA segment encoding the desired FGFR extracellular domains will be ligated in frame to the 5' end of a DNA segment encoding the desired oligomerization domain, such that a contiguous fusion protein is produced upon expression of the ligated DNA. These strategies may encompass PCR techniques in obtaining or modifying pertinent DNA segments. Also available to one of ordinary skill in the art is a variety of host cells for containing and expressing the desired constructs.

Constructs include native sequences and variants, as well as sequences that hybridize under stringent conditions.

Methods of Using FGFR-Ig Fusions

Working examples of the invention provide methods of inhibiting FGF-stimulated cell proliferation by administering an FGFR antagonist comprising a fusion of the extracellular domain of FGFR with the Fc region of an Ig molecule as the heterologous oligomerization domain in an amount effective to inhibit the proliferation. The invention also provides methods of inhibiting angiogenesis by administering to cells capable of undergoing angiogenesis the fusion protein in an amount effective to inhibit angiogenesis. The inhibition could be in vitro or in vivo.

"Amount effective to inhibit" is intended to mean that amount of the fusion protein which prevents or induces a measurable inhibition of FGF-stimulated cell proliferation. Methods of measuring such inhibition are known to those skilled in the art and include available commercial kits which are based on measuring numbers of viable cells.

Where the inhibition is in vivo, the amount effective to inhibit can induce a concentration of the fusion protein in the target organ or tissue needed to inhibit cell proliferation in the cells of the target organ or tissue.

The invention provides methods of treating disorders which are FGF-mediated, FGFR-mediated or angiogenesis-mediated. The methods encompass administering therapeutically effective amounts of the polypeptides of the invention or vectors comprising polynucleotides encoding the polypeptides of the invention to a mammal. The administration can be alone or in conjunction with other agents, including other inhibitors of angiogenesis, tumorigenesis, anticancer agents and the like.

Where the treating of a disorder involves administering polynucleotides comprising coding regions comprising the polypeptides of the invention, the polynucleotides are provided in expression vectors capable of expressing the polynucleotides in a particular organism, organ, tissue, or cell type; such that the coding region is operably linked to the promoter of the expression vector.

The therapeutic polynucleotides and polypeptides of the present invention may be utilized in gene delivery vehicles. The gene delivery vehicle may be of viral or non-viral origin (see generally, Jolly, Cancer Gene Therapy (1994) 1:51-64; Kimura, Human Gene Therapy (1994) 5:845–852; Connelly, Human Gene Therapy (1995) 1:185–193; and Kaplitt, Nature Genetics (1994) 6:148–153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5,219,740; WO 93/11230; WO 93/10218; Vile and Hart, *Cancer Res.* (1993) 53:3860–3864; Vile and Hart, *Cancer Res.* (1993) 53:962–967; Ram et al., Cancer Res. (1993)53:83–88; Takamiya et al.,J Neurosci. Res. (1992) 33:493–503; Baba et al., *J. Neurosurg.* (1993) 79:729–735; U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J Vir.* (1989) 63:3822–3828; Mendelson et al., *Virol.* (1988) 166:154–165; and Flotte et al., PNAS(1993) 90:10613–10617.

Representative examples of adenoviral vectors include those described by Berkner, *Biotechniques* (1988) 6:616–627; Rosenfeld et al., *Science* (1991) 252:431–434; WO 93/19191; Kolls et al., PNAS(1994) 91:215–219; Kass-Eisler et al., PNAS (1993) 90:11498–11502; Guzman et al., *Circulation* (1993) 88:2838–2848; Guzman et al., *Cir. Res.* (1993) 73:1202–1207; Zabner et al., *Cell* (1993) 75:207–216; Li et al., *Hum. Gene Ther.* (1993) 4:403–409; Cailaud et al., *Eur. J Neurosci.* (1993) 5:1287–1291; Vincent et al., *Nat. Genet.* (1993) 5:130–134; Jaffe et al., *Nat. Genet.* (1992) 1:372–378; and Levrero et al., *Gene* (1991) 101:195–202. Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* (1 992) 3:147–154 may be employed.

Other gene delivery vehicles and methods may be employed, including polycationic condensed DNA linked or unlinked to killed adenovirus alone, for example Curiel, *Hum. Gene Ther.* (1992) 3:147–154; ligand linked DNA, for example see Wu, *J Biol. Chem.* (1989) 264:16985–16987; eukaryotic cell delivery vehicles cells, for example see U.S. Serial No. 08/240,030, filed May 9, 1994, and U.S. Serial No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* (1994) 14:2411–2418, and in Woffendin, *Proc. Nat. Acad. Sci.* (1994) 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422, 120, PCT Nos. WO 95/13796, WO 94/23697, and WO 91/14445, and EP No. 0 524 968.

Further non-viral delivery suitable for use includes mechanical delivery systems such as the approach described in Woffendin et al., *Proc. Natl. Acad. Sci. USA* (1994) 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

The invention also provides a method of diagnosing disorders involving FGF-stimulated cell proliferation, angiogenesis and tumorigenesis.

In one embodiment, the method encompasses administering to test cells an effective amount of the fusion proteins of the invention and assessing inhibition compared to a control.

In another embodiment of the invention, the above-described methods of diagnosis encompass in vitro administration of any of the described fusion protein antagonists to cells in culture.

In another embodiment of the invention, the above-described methods of diagnosis involve administering any of the described fusion proteins in vivo.

In one embodiment, therapeutically effective amounts of pharmacological compositions containing fusion protein antagonists as described herein are administered to a patient or an animal model in need of such administration. The methods of treatment or prevention encompass administering effective amounts of a pharmacological composition containing a fusion protein of the invention as described herein.

Methods of constructing therapeutically effective fusion protein antagonists are provided. In one embodiment of the invention, binding affinities and specificities of the fusion proteins are first characterized in vitro. Next, proteins with desired affinities and specificities against various forms of FGF are selected and further assessed for inhibition of FGF-stimulated cell proliferation. Next, new fusion proteins are constructed by deletion of segments determined not to be necessary for desired affinities and specificities of binding to FGF or high potency of inhibition of FGF-stimulated cell proliferation. The above described assessments and selections are repeated with the smaller deletion constructs; until a minimal protein structure having the desired affinities, specificities and potencies is constructed. The therapeutic effectiveness of selected minimal constructs are then assessed in vivo.

The administration includes, but is not limited to, administration to animal models and patients manifesting the following disorders: restenosis after angioplasty or atherectomy (Wilcox, J. N. (1993) *Am J Cardiol* 72: 88E–95E), ophthalmological disorders involving excessive vasoproliferation (Gariano et al. (1996) *Survey Ophthalm.* 40: 481–490), various tumors and cancers (Kim et al. (1993) *Nature* 334: 841–844; Kim et al. (1993) *Nature* 362: 841–844; Min et aL (1996) *Cancer Res.* 56: 2428–2433) including AIDS-related Kaposi sarcoma. Pontaliano et al. (1994) *Biochemistry* 33: 10229–10248.

Pharmacological Compositions

The invention provides pharmacological compositions comprising the fusion polypeptides of the invention or polynucleotides encoding the polypeptides described herein. The pharmacological compositions may also contain any of the described variants of FGFR.

Compounds useful for formulating polypeptides and/or protein pharmaceutical compositions can be used with fusion proteins.

The pharmaceutical compositions will comprise a therapeutically effective amount of any of the proteins of the claimed invention.

The term "therapeutically effective amount" as used herein refers to an amount of a therapeutic agent to treat or prevent a disorder sufficient to exhibit a detectable preventive, ameliorative, curative or other therapeutic effect. The effect may include, for example, treatment, amelioration, or prevention of any physical or biochemical condition, for example, including but not limited to hyperproliferative growth, angiogenesis and cancer.

The effect can be detected by, for example, biochemical or histological means of assessing angiogenesis. Therapeutic effects also include reduction in physical symptoms, such as decreased tumor size. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation.

In this aspect of the invention, by "FGF-mediated disorder", "FGFR-mediated disorder" or "angiogenesis-mediated disorder" is intended an adverse biological or biochemical condition that is exacerbated by FGF, FGFR or angiogenesis. Examples of such disorders include, but are not limited to, tumorigenesis, neovascularization, hyperproliferation of vascular smooth muscle cells, and the like.

Tumors include, but are not limited to, bladder, breast, node-negative breast, lung, rectal, colorectal, testis, and cervical tumors; glioblastoma; childhood brain tumors, squamous cancer of the tongue, etc.

Disorders involving neovascularization include, but are not limited to, diabetic retinopathy, retinopathy of prematurity (ROP), choroidal neovascularization, neovascular glaucoma, wound healing after surgery and injury, corneal scarring, ocular neoplasia, breakdown of blood-retina barrier.

Disorders involving hyperproliferation of vascular smooth muscle cells include, but are not limited to, postangioplasty and postatherectomy restenosis.

It is recognized that depending on the type and stage of a particular disorder, the disorder may be mediated by FGF, FGFR, angiogenesis, or combinations thereof.

For purposes of the present invention, an effective dose will be from about 1 pg/kg to 10 mg/kg of the fusion protein in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid coknown to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients are available in *Remington's Pharmaceutical Sciences* (Mack Pub. Co., NJ 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Administration Methods

Once formulated, the fusion protein compositions of the invention can be (1) administered directly to the subject; or delivered ex vivo, to cells derived from the subject.

Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Additional pharmaceutical methods may be employed to control the duration of action. Controlled release preparations may be achieved by the use of polymers to complex or absorb the compositions. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric Osubstance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly (methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980).

A preferred controlled release composition for delivery of such compositions will encompass liposome encapsulation as described in, but not limited to U.S. Pat. No. 4,522,803; EP 0 280 503 B1 and WO 95/13796.

Detecting Cell Proliferation

The invention provides methods of diagnosing FGF-stimulated cell proliferation and angiogenesis by administering to test cells an effective amount of any of the fusion proteins and assessing inhibition against a control. The cells can be in vivo or in vitro. In this aspect, the administration could be directed at animal models or patients, including those described above, or directed at primary cultures or cell lines derived from tissues affected by disease states potentially involving FGF-stimulation. The method of diagnosis is, thus, useful for determining the propensity of an animal to respond to treatment with fusion protein antagonists as provided by the invention.

In this manner, the invention relates to providing receptor oligomer fusion constructs which can effect clinically determinable inhibition of angiogenesis or diseases involving angiogenesis when administered in effective amounts to patients or animal models in need of such administration.

Experimental

FGFR-Ig Fc fusion protein dimer (FGFR ECD Ig), according to Construct #1 (Example 6) was characterized with respect to bFGF binding in vitro (FIG. 1) and in whole cells (FIG. 2). Determined $IC_{50}$ values indicate that the dimerized receptor is an effective antagonist of FGF binding at subnanomolar concentrations, and is 20–50 fold more potent than the monomeric form (FGFR ECD mono) in competing for bFGF binding.

EXAMPLE 1

Figure 1:
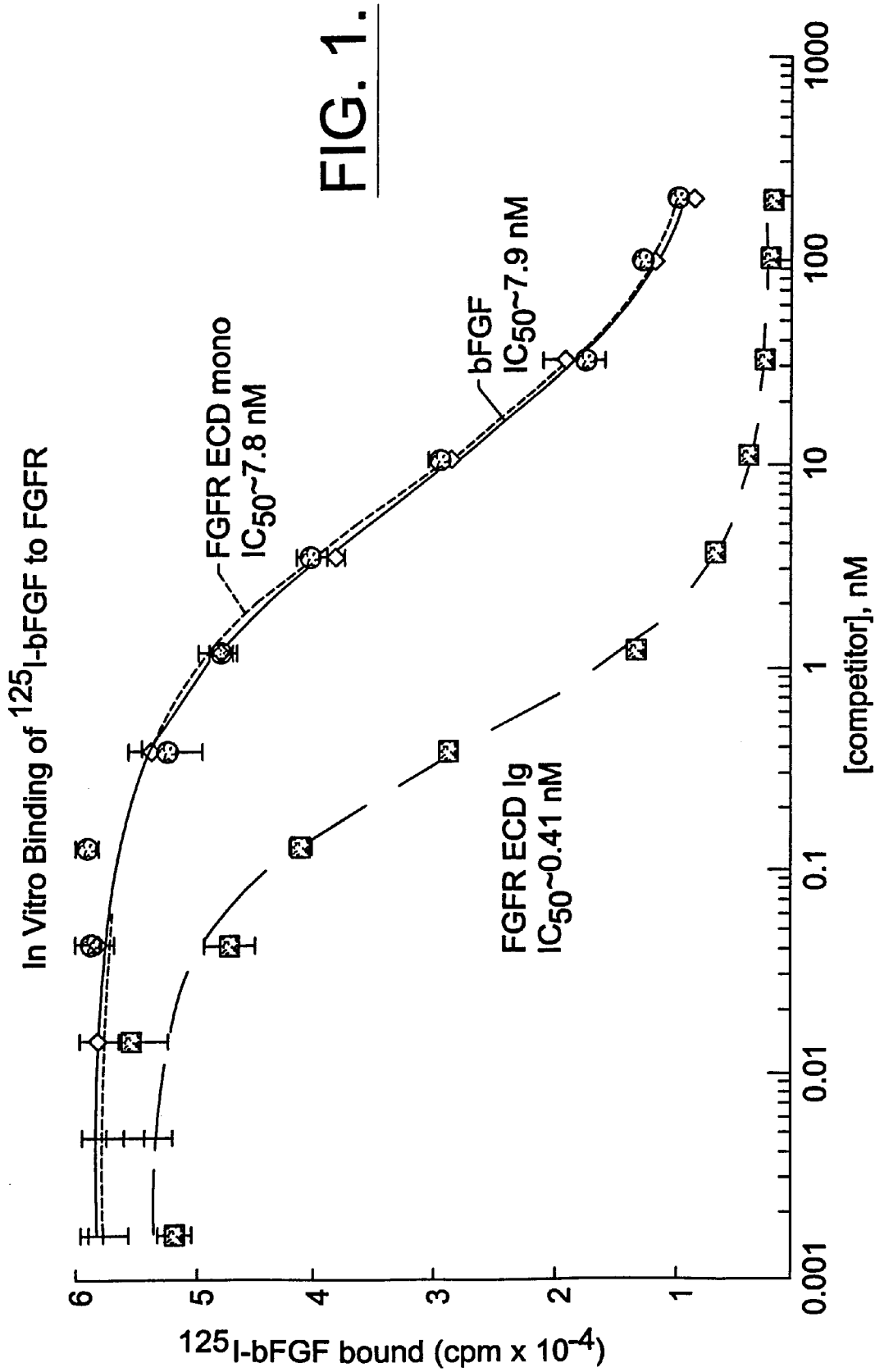
FIG. 1 depicts in vitro binding of $^{125}$I-bFGF to FGFR.

In Vitro Binding of $^{125}$I-bFGF to FGFR (FIG. 1).

FGFR monomer (U.S. Pat. No. 5,229,501) and FGFR-Ig Fc fusion dimer according to Construct #1 (Example 6) were tested for their ability to compete with $^{125}$I-bFGF for binding to immobilized FGF receptors. Immulon 2 microtiter plates were coated with 10 nM FGFR-IgFc fusion protein (construct 1) in 50 mM $Na_2CO_3$, pH 9.6 overnight at 4° C. The plates were then blocked with 1% gelatin in Dulbecco's PBS (DPBS) for 1 hr at room temperature, and washed with DPBS plus 0.05% Tween 20. Serial dilutions in duplicate of FGFR-Ig fusion dimer (Construct #1, Example 6), FGFR monomer, or bFGF were added, followed by a subsaturating amount (0.5 nM final) $^{125}$I-bFGF in DPBS plus 0.1% gelatin, 0.1% triton X-100 and 10 $\mu$M Heparin, pH 7.75. After 2 hr at room temperature, wells were washed and the bound radioactivity determined by gamma counting. Displacement curves were analyzed with a four parameter fit to obtain $IC_{50}$ values. The results indicate that the FGFR-Ig Fc fusion dimer is active as a FGF antagonist at subnanomolar concentrations, and is approximately 20-fold more potent than the FGFR monomer protein as a competitor of bFGF binding to immobilized FGF receptors.

EXAMPLE 2

Binding of $^{125}$I-bFGF to FGFR: Whole Cells (FIG. 2).

FGFR monomer (U.S. Pat. No. 5,229,501) and FGFR-Ig fusion dimer according to Construct #1 (Example 6) were tested for their ability to compete with $^{125}$I-bFGF for binding to stable HEK293 cell lines overexpressing FGFR1. FGFR was overexpressed ($0.3 \times 10^6$ receptors/cell) in HEK293 cells by transfection of the FGFR1 cDNA (U.S. Pat. No. 5,229,501) in the high copy number plasmid pCDNA3 and selecting clones resistant to G418. $1.5 \times 10^5$ cells were plated in 24 well plates in DMEM plus 10% serum. Following overnight incubation, the cells were washed twice with 1 ml DMEM plus 0.2% gelatin and 15 units/ml heparin. Serial dilutions of FGFR extracellular domain-Fg Fc fusion dimer, FGFR monomer, or bFGF were pre-mixed with 0.1 nM $^{125}$I-bFGF (1138 Ci/mmol) and 250 $\mu$l of this mixture was added to each well, and incubated at 37° C. for 30 minutes. The media was removed, and the cells washed three times with 1 ml DMEM containing 150 mM NaCl, 0.2% gelatin, and 15 units/ml heparin. The cells were lysed in 250 $\mu$l 0. 1% SDS and lysates counted in a gamma counter. Displacement curves were analyzed with a four parameter fit to obtain $IC_{50}$ values. In this assay, the FGFR-Ig fusion dimer is approximately 50-fold more potent than the FGFR monomer protein as a competitor of bFGF binding to cells.

EXAMPLE 3 bFGF/Serum Stimulated HUVEC Proliferation (FIG. 3)

FGFR-Ig fusion dimer (FGFR ECD Ig), according to Construct #1 (Example 6) was tested for its ability to inhibit proliferation of human umbilical vein endothelial cells (HUVEC) in serum- and bFGF-containing media. HUVEC cells were plated in gelatin coated 96-well plates at a density of 2000 cells/well in 50 $\mu$l of EBM (endothelial basal media-Clonetics). The cells were incubated overnight (37° C. 5% $Co_2$), the media was removed and 200 $\mu$l of media was added containing 10 ng/ml bFGF+90 $\mu$g/ml heparin+ either 2% or 5% FBS and +/−0.1 $\mu$M FGFR fusion (construct 1). The FGFR fusion was preincubated with bFGF and heparin for at least 30 minutes prior to addition to cell wells. Proliferation indexes were determined on days 0,1,2,3,4 and 5 using the WST-1 cell proliferation assay (Boehringer Mannheim) which measures number of viable cells. 100 nM FGFR-Ig fusion dimer completely inhibits bFGF-stimulated HUVEC proliferation, even in the presence of 5% serum.

EXAMPLE 4

HUVEC (Proliferation: Comparison of FGFR Monomer and FGFR-Ig Dimer FIG. 4)

FGFR monomer (U.S. Pat. No. 5,229,501) and FGFR-Ig fusion dimer (FGFR ECD Ig), according to Construct #1 (Example 6) were compared for their ability to inhibit HUVEC proliferation at different doses in the presence of 10 ng/ml bFGF+90 $\mu$g/ml heparin+5% FBS as described in Example 3 above. The FGFR-Ig fusion dimer is more than 10-fold more potent than the FGFR monomer as an inhibitor of HUVEC proliferation in the presence of serum and bFGF, can inhibit proliferation completely, and can inhibit proliferation even below the level seen in the absence of FGF. These results are consistent with the data from in vitro and whole-cell binding assays of FIGS. 1–3.

FIGS. 3 and 4 indicate that not only FGFR-Ig is a more potent inhibitor of this proliferation than monomeric extracellular domains of FGFR, the fusion protein is capable of 100% inhibition of the proliferation.

EXAMPLE 5

Comparison of FGFR-Ig to Anti-bFGF Mab (FIG. 5)

The ability of the FGFR-Ig fusion dimer (FGFR ECD Ig), according to Construct #1 (Example 6) to compete with $^{125}$I-bFGF for binding to immobilized receptors was compared to the highest affinity neutralizing mouse monoclonal antibody to bFGF which is available (Upstate Biotechnology Inc). The assay was performed as in (A). The overall $IC_{50}$s for these two protein is similar, but the antibody displays some non-competitive binding behavior, and is unable to completely inhibit $^{125}$I-bFGF binding, even at high concentrations. In contrast, the FGFR-Ig fusion protein completely inhibits binding.

EXAMPLE 6

FGFR Extracellular Domain-Ig Fc Fusion Constructs

SEQ ID NOS:1–12 set forth nucleotide and amino acid sequences for fusion protein Constructs 1–6 comprising segments of an FGFR extracellular domain fused to the Fc region of an immunoglobulin molecule.

Construct #1

The polynucleotide and amino acid sequences of construct #1 are set forth in SEQ ID NOS:1 and 2, respectively.

Construct #1 contains, in order from the 5'/NH2-terminus to the 3'/COOH-terminus: human FGFR1 signal peptide (comprised by amino acids 1–21); human FGFR1 extracellular domain (nucleotides 64–1123, amino acids 22–374) which contains the Ig I segment (comprised by nucleotides 163–303, amino acids 55–101), the acid box segment (nucleotides 376–399, amino acids 126–133), the Ig II segment (nucleotides 526–684, amino acids 176–228), and the IIIc variant of Ig III segment (nucleotides 823–1017, amino acids 275–339); a linker sequence with a thrombin cleavage site (nucleotides 1123–1170, amino acids 375–390); and the Fc portion of human IgG1 which includes the hinge region, and domains CH2 and CH3 (nucleotides 1171–1869, amino acids 391–622).

Construct #2

The polynucleotide and amino acid sequences of construct #2 are set forth in SEQ ID NOS:3 and 4, respectively.

Construct #2 comprises deleting from construct #1 the Ig I segment plus additional flanking sequences (nucleotides 91–357, amino acids 31–119, as numbered in construct #1), and part of the linker encompassing the thrombin cleavage site (nucleotides 1123–1146, amino acids 375–382, as numbered in construct #1).

Accordingly, construct #2 comprises from the 5'/NH2-terminus to the 3'/COOH-terminus: human FGFR1 signal peptide, human FGFR1 extracellular domain which contains the acid box segment, the Ig II segment and the IIIc variant of Ig III segment; and the Fc portion of human IgG1 which includes the hinge region, and domains CH2 and CH3.

Construct #3

The polynucleotide and amino acid sequences of construct #3 are set forth in SEQ ID NOS:5 and 6, respectively.

Construct #3 comprises deleting from construct #1 the Ig I segment as well as the acid box and flanking sequences (nucleotides 91–441, amino acids 31–147, as numbered in construct #1), and part of the linker encompassing the thrombin cleavage site (nucleotides 1123–1146, amino acids 375–382, as numbered in construct #1).

Accordingly, construct #3 comprises from the 5'/NH2-terminus to the 3'/COOH-terminus: human FGFR1 signal peptide, human FGFR1 extracellular domain which contains the Ig II segment and the IIIc variant of the Ig III segment; and the Fc portion of human IgG1 which includes the hinge region, and domains CH2 and CH3.

Construct #4

The polynucleotide and amino acid sequences of construct #4 are set forth in SEQ ID NOS:7 and 8, respectively.

Construct #4 is the same as construct #2 with two additional changes:
a) Nucleotides 937 to 938 were changed from "CT" to "GA" which changes amino acid 313 from LEU to GLU (as numbered in constructs #2 and 4). This mutation decreases the affinity of the Fc portion for Fc receptors.
b) Nucleotide 1225 was changed from "C" to "T", which changes amino acid 409 from PRO to SER. (as numbered in sequences #2 and 4). This mutation decreases the affinity of the Fc portion for complement.

The positions correspond to amino acids 235 (LEU to GLU) and 331 (Pro to Ser) of human IgGl.

Construct #5

The polynucleotide and amino acid sequences of construct #5 are set forth in SEQ ID NOS:9 and 10, respectively.

Construct #5 is the same as construct #3 with two additional changes:
a) Nucleotides 853 to 854 have been changed from "CT" to "GA" which changes amino acid 285 from LEU to GLU (as numbered in sequences #3 and 5).
b) Nucleotide 1141 has been changed from "C" to "T", which changes amino acid 385 from PRO to SER.

The positions changed correspond to amino acids 235 (LEU to GLU) and 331 (Pro to Ser) of human IgGI, and result in decreased affinities of the Fc portion for Fc receptors and complement respectively.

Construct #6

The polynucleotide and amino acid sequences of construct #6 are set forth in SEQ ID NOS:11 and 12, respectively.

Construct #6 is the same as construct #5 with one change: Nucleotides 772–798 (amino acids 258–266), as numbered in construct #5, were deleted. Thus, this construct lacks all the residues from the linker sequence encompassing the thrombin cleavage site as described in construct #1, and is potentially the least immunogenic construct.

The purpose of this construct was to eliminate all residual amino acids left over from the original linker segment in construct #1. Construct #6 has the same activity as the other constructs and is the preferred construct for administration as a therapeutic, because it is potentially the least immunogenic construct.

Other modifications and embodiments of the invention will come to mind in one skilled in the art to which this invention pertains having the benefit of the teachings presented herein. Therefore, it is to be understood that the invention is not to be limited to the specific embodiments disclosed. Although specific terms are employed, they are used in generic and descriptive sense only and not for purposes of limitation, and that modifications and embodiments are intended to be included within the scope of the appended claims.

That which is claimed:

1. A fusion polypeptide comprising a fibroblast growth factor (FGF) receptor extracellular domain fused to a heterologous oligomerization domain wherein said extracellular domain comprises the acid box and lacks the Ig I segment, and wherein said heterologous oligomerization domain is the Fc region of an immunoglobulin class G molecule, wherein said FGF receptor is human FGFR1.

2. A fusion polypeptide having the amino acid sequence selected from the group consisting of:
   a) the amino acid sequence set forth in SEQ ID NO:2;
   b) an amino acid sequence having at least 75% identity to the amino acid sequence set forth in SEQ ID NO:2; and
   c) an amino acid sequence having at least 95% identity to the amino acid sequence set forth in SEQ ID NO:2,
wherein said polypeptide comprises the acid box set forth as amino acid residues 126–133 of SEQ ID NO:2 and is capable of binding FGF.

3. A polynucleotide construct encoding said amino acid sequence of claim 2.

4. A polynucleotide construct having the sequence selected from the group consisting of:
   a) the nucleotide sequence set forth in SEQ ID NO:1;
   b) a nucleotide sequence having at least 75% identity to the nucleotide sequence set forth in SEQ ID NO:1; and
   c) a nucleolide sequence having at least 95% identity to the nucleotide sequence set forth in SEQ ID NO:1,
wherein said polylnucleotidc construct encodes a fusion polypeptide that comprises the acid box set forth as amino acid residues 126–133 of SEQ ID NO:2 and is capable of binding FGF.

5. A polynucleotide construct encoding the polypeptide of claim 1.

6. A viral vector comprising the polynucleotide construct of claim 5.

7. An isolated host cell containing or capable of expressing the polynucleotide construct of claim 5.

8. The polypeptide of claim 1, wherein said oligomerization domain is capable of forming an oligomer that is at least a dimer with at least one other polypeptide comprising said oligomerization domain of claim 1.

9. The polypeptide of claim 8, wherein said oligomer is a homodimer.

10. The polypeptide of claim 8, wherein said oligomer is a heterodimer.

11. The polypeptide of claim 1, wherein said polypeptide is capable of binding FGF.

12. The polypeptide of claim 1, wherein said immunoglobulin is human immunoglobulin.

13. The polypeptide of claim 1, further comprising a variant of the Ig III segment of said extracellular domain.

* * * * *